US005378806A

United States Patent [19]

Willis

[11] Patent Number: 5,378,806

[45] Date of Patent: Jan. 3, 1995

[54] FUSION PROTEIN PRODUCED BY RETROVIRUS-MEDIATED SECRETION

[75] Inventor: John W. Willis, Shreveport, La.

[73] Assignee: Research Corporation Technologies, Inc., Tucson, Ariz.

[21] Appl. No.: 881,585

[22] Filed: May 12, 1992

Related U.S. Application Data

[60] Division of Ser. No. 522,428, May 11, 1990, Pat. No. 5,175,099, which is a continuation-in-part of Ser. No. 353,293, May 17, 1989, abandoned.

[51] Int. Cl.$^6$ .............................................. C07K 13/00

[52] U.S. Cl. .................................. 530/350; 435/64.7; 536/23.4; 530/412

[58] Field of Search ................ 435/64.7; 530/350, 412

[56] References Cited

U.S. PATENT DOCUMENTS

| | | | |
|---|---|---|---|
| 4,751,180 | 6/1988 | Cousens et al. | 435/64.7 |
| 4,828,987 | 5/1989 | Kopchick et al. | 435/69.4 |
| 4,861,719 | 8/1989 | Miller | 435/236 |
| 4,918,166 | 4/1990 | Kingsman et al. | 530/350 |

OTHER PUBLICATIONS

Adams et al. (1987) "The Expression of Hybrid HIV:Ty Virus-Like Particles in Yeast", *Nature* 329, 68–70.

Crawford et al. (1985) "A Deletion Mutation in the 5' Part of the pol Gene of Moloney Mruine Leukemia Virus Blocks Proteolytic Processing of the gag and pol Polyproteins", *Journal of Virology* 53, 899–907.

Delchambre et al. (1989) "The GAG Precursor of Simian Immunodeficiency Virus Assembles into Virus—Like Particles", *The EMBO Journal* 8, 2653–2660.

Felsenstein et al. (1988) "Expression of the gag-pol Fusion of Moloney Murine Leukemia Virus Without gag Protein does not Induce Virion Formation or Proteolytic Processing", Journal of Virology 62, 2179–2182.

LeGrice et al. (1988) "Active Site Mutagenesis of the AIDS Virus Protease and its Alleviation by trans Complementation", *The EMBO Journal* 7, 2547–2553.

Rhee et al. (1987) "Myristylation is Required for Intracellular Transport but not for Assembly of D-Type Retrovirus Capsids", *Journal of Virology* 61, 1045–1053.

Schultz et al. (1988) "Fatty Acylation of Proteins" *Ann. Rev. Cell Biol.* 4, 611–647.

Voynow et al. (1985) "Truncated gag-Related Proteins are Produced by Large Deletion Mutants of Rous Sarcoma Virus and Form Virus Particles", *Journal of Virology* 55, 79–85.

Weighous et al. (1986) "Secretion of Enzymatically Active Human Renin From Mammalian Cells using an Avian Retroviral Vector", *Gene* 45, 121–129.

Wills et al. (1989) "Creation and Expression of Myristylated Forms of Rous Sarcoma Virus Gag Protein in Mammalian Cells", *Journal of Virology* 63, 4331–4343.

*Primary Examiner*—Robert J. Hill, Jr.
*Assistant Examiner*—John D. Ulm
*Attorney, Agent, or Firm*—Scully, Scott, Murphy & Presser

[57] ABSTRACT

The present invention is directed to replicable expression vectors for producing fusion proteins which are secreted in membraneous particles budded from the cell membrane. In particular these vectors express a hybrid gene product composed of a modified retrovirus gag gene fused to a heterologous gene, or any part thereof, wherein the gag gene modification is sufficient to enable a cell to produce the hybrid gene product in a membraneous particle by budding from the cell membrane into the culture medium or extracellular space, a process known as retrovirus-mediated secretion. The minimum gag sequences needed to obtain particle formation are described. The invention also provides hosts containing the expression vectors, and the fusion proteins produced by the vectors. Further the invention provides the membraneous particles produced by retrovirus-mediated secretion and uses of these particles for protein purification and in therapeutics.

7 Claims, 16 Drawing Sheets

FUSION PROTEIN PRODUCED BY RETROVIRUS-MEDIATED SECRETION

This invention was made with Government support under SR29-CA-47482-03 awarded by the National Institutes of Health. The Government has certain rights in the invention.

This is a divisional of copending application Ser. No. 522,428, now U.S. Pat. No. 5,175,099, filed on May 11, 1990 which is a continuation-in-part of U.S. Ser. No. 353,293 filed May 17, 1989 abandoned.

FIELD OF THE INVENTION

This invention is directed to replicable expression vectors and an expression system for producing recombinant fusion proteins in membraneous particles which are secreted from a cell. This process is driven by a modified retrovirus Gag domain that forms a part of the fusion protein. The membraneous particles produced by the instant expression system are useful in facilitating purification of the fusion protein, in producing vaccines as well as in other therapeutic applications.

BACKGROUND OF THE INVENTION

Retroviruses are small, membrane-enveloped RNA viruses that were first discovered over 80 years ago. They have been extensively studied because of their importance in helping understand eukaryotic gene expression, their role in elucidating cellular growth factors and oncogenes, their role as human pathogens (particularly in AIDS), and their use as tools to genetically alter host cells, especially for experimental and therapeutic purposes. (Retrovirology is reviewed by Varmus, 1984, *Science* 240: 1427–1435). The retrovirus life cycle involves 1) attachment to a host cell via specific receptors, 2) entry into the host, 3) replication of the genomic RNA via a DNA intermediate which then integrates into the host chromosome, 4) transcription and translation of virion genes, 5) assembly of viral components into virion particles and 6) budding of the particles from the plasma membrane. When the virion particle buds from the cell surface, it becomes membrane-enveloped.

The cell entry step of the retrovirus life cycle only partly determines the host range of a given retrovirus. It has long been established that arian retroviruses can infect and transform mammalian cells, but do not release infectious or non-infectious virus particles [reviewed by Weiss, 1984 in "RNA Tumor Viruses," 2nd ed., Vol. 1 (Weiss, Teich, Varmus and Coffin, eds.) Cold Spring Harbor Laboratory, Cold Spring Harbor, N.Y., p. 209–260]. For avian Rous sarcoma virus (RSV) the block to particle release appears to occur during virion assembly and budding and that block involves the gag gene product, $Pr76^{gag}$ [Vogt et al. 1982, J. Virol. 44: 725–730].

The gag gene (which encodes five RSV structural proteins) is one of three genes common to all replication-competent retroviruses, the others being pol (which codes for the reverse transcriptase and related functions) and env (which codes for the envelope glycoproteins). RSV is unique in that it also carries an oncogene, src in addition to these three structural genes. The entire nucleotide sequence of RSV is known (Schwartz et al., 1983, Cell 32: 853–869). A large body of genetic evidence, obtained through the characterization of spontaneous mutations, has suggested that gag is the only viral gene needed for budding and particle formation (reviewed in Dickson et al. 1984, in "RNA Tumor Viruses," op. cit., p. 513–648). That is, non-infectious particles can be released from the cells in the absence of reverse transcriptase, envelope glycoproteins, tumor-inducing protein or genomic RNA. It is only when gag is mutated that the ability to form particles is lost.

$Pr76^{gag}$ is a polyprotein precursor which is synthesized on cytoplasmic ribosomes from an unspliced, proviral transcript that is identical to the viral genome. This polyprotein is subsequently targeted to the plasma membrane (the site of virus assembly) by a mechanism that is not presently understood. Like all type C retroviruses, RSV does not pre-assemble core structures in the cytoplasm, but rather these structures arise concurrently with the envelopment or budding process. The five internal virion proteins that arise through proteolytic processing of $Pr76^{gag}$ are designated as follows according to their order in the precursor: $NH_2$-p19 (the matrix or membrane-associated protein, MA), p2 and p10 (both of unknown function), p27 (the capsid protein, CA), p12 (the nucleocapsid, NC) and p15-COOH (the protease, PR). As is the case for other retroviruses, the processing of $Pr76^{gag}$ is poorly understood, but it is believed to occur after the arrival of the precursor at the plasma membrane. However, processing itself does not appear to be a prerequisite to the budding process, since RSV mutants have been found that synthesize truncated forms of $Pr76^{gag}$ which are not cleaved but are released from the cells in the form of particles (Voynow and Coffin, 1985, J. Virol. 55: 79–85). Mammalian retrovirus processing and budding is also independent of mammalian gag precursor cleavage (Crawford et al. 1985. J. Virol. 53: 899–907).

It is not clear how retroviruses target their gag products to the plasma membrane, though it is widely believed that the MA protein plays a critical role. In the case of mammalian retroviruses, almost all encode Gag proteins having a 14-carbon fatty acid, myristate, at the amino-terminus, and this hydrophobic moiety may play a role in membrane interactions during targeting. The myristic acid addition appears to occur co-transitionally, and results in an amide bond between the acyl group and the α-amino group of glycine following removal of the initiation methionine (reviewed by Schultz et al., 1988, Ann. Rev. Cell Biol. 4: 611–647). Elimination of the myristic acid addition site on the Gag protein of Mason-Pfizer monkey virus (M-PMV) by means of site-specific mutagenesis abrogates M-PMV particle release and Gag precursor processing (Rhee et al. 1987, J. Virol. 61: 1045–1053); similar results have been found for murine leukemia virus (MuLV; Rein et al. 1986, Proc. Natl. Acad. Sci. USA 83: 7246–7250).

The RSV Gag protein does not have glycine at position 2 and is not myristylated; hence, the failure of $Pr76^{gag}$ to be targeted, processed and released by budding from mammalian cells might be due to a requirement for myristic acid addition. In accordance with the present invention, it was discovered that the block to RSV $Pr76^{gag}$ function in mammalian cells is alleviated by the creation of an amino-terminal myristic acid addition site. Myristic acid addition does not adversely affect particle formation in avian cells; in fact it appears to augment particle formation. Furthermore, it was surprisingly found that low, but easily detected, levels of particle formation occur when the wild type (unmodified) Pr76 is expressed at unusually high levels in mammalian cells by the SV40-based expression vectors of the present invention.

It was also discovered in accordance with the present invention that C-terminal deletions of myristylated $Pr76^{gag}$ result in a protein that is still processed and budded from a mammalian cell as is full-size, myristylated $Pr76^{gag}$. Furthermore, the present invention provided the surprising discovery that heterologous gene sequences can be fused to truncated, myristylated $Pr76^{gag}$, and the resulting fusion proteins will be processed and budded from a mammalian or avian cell in membrane-enveloped particles similar to immature virions. This process is known as retrovirus-mediated secretion and provides a method for releasing proteins packaged in membrane-enveloped particles, or membrane vesicles, into the culture medium. The particles can be easily and rapidly collected from the medium by centrifugation, and thus provide a convenient means of obtaining recombinant proteins for rapid purification.

In further investigations it has been discovered that three regions of Gag appear to promote budding. This finding allows construction of fusion proteins in accordance with the present invention which have a minimal amount of the Gag protein needed to enable a cell to produce the fusion protein in a membraneous particle. Specifically, it has been discovered that the three regions of Gag needed for budding and particle formation are amino acids 1–8 (the myristylation site), amino acids 84–174 (from MA and the small p2 domain), and amino acids 417–515 (from CA and NC). However, it is possible that some of these residues are not essential for budding and particle formation and thus even smaller regions of Gag may be used in fusion protein constructs.

Retrovirus-based expression systems are known and are reviewed by Varmus. Some of the systems secrete proteins in soluble form into the culture medium. That is, the secretion occurs via the normal intracellular pathway and the secreted proteins are not contained in membrane vesicles or particles, for example, Weighous et al. 1986, Gene 45: 121–129. Further gag gene fusions to other retrovirus genes, such as env, pol, onc (oncogenes, e.g. src) are part of the life cycle of all retroviruses. At present none of these gag retrovirus fusions are known to bud (Felsenstein et al. 1988, J. Virol. 62: 2179–2182).

Adams et al. 1987, Nature 329: 68–70, describe fusions of foreign proteins to the yeast TYA gene, a retrotransposon gene homologous to the retrovirus gag gene. Yeast retrotransposons (Ty) form virus-like particles (Ty-VLPs) in a manner analogous to virion formation in retroviruses; however, unlike retroviruses, Ty-VLPs are not budded from the cell, but rather accumulate intracellularly. Like retroviruses, Ty-VLPs are membrane-enveloped particles that do not require cleavage of TYA for production of Ty-VLPs. The mechanism of Ty-VLP particle production is not known. Ty-VLPs are not readily purified. Their purification requires lysing the cells and differential centrifugation to separate cellular components from Ty-VLPs.

In contrast, to Ty-VLPs, the present invention is directed to retrovirus gag fusions with heterologous genes whose products are then exported or secreted, from the cell by the viral budding process. In this process the fusion protein continuously accumulates in the culture medium or extracellular space in membraneous particles. Unlike Ty-VLPs, these particles are readily purified; they are also useful for rapid purification of the fusion protein, as immunogens and as drug delivery systems.

The membraneous particles have several advantages for production of fusion proteins. Because of their large size, the particles are easily pelleted upon centrifugation and thus separated from soluble components in the culture medium. Fusion proteins, or any protein, secreted into the culture via the normal intracellular path cannot be rapidly pelleted. Hence, it is more difficult to separate normally secreted proteins (i.e., not in a particle) from those secreted in a membraneous particle. Further, purification of the fusion protein from the membraneous particle is rapid, since the particles have relatively few components. Additionally, the expression system is highly efficient and allows continual production of the membraneous particles since particle production is not toxic to the cells. In the case of RSV gag fusions expressed in mammalian cells, they were found to have a half-time of about 30 minutes for passage through the cell and release in membraneous particles. Finally, the particles are safe to work with, since they lack a full retrovirus genome and are, therefore, noninfectious.

SUMMARY OF THE INVENTION

The present invention is directed to replicable expression vectors for producing fusion proteins which are secreted in membraneous particles budded from the cell membrane. In particular these vectors express a hybrid gene product composed of a modified retrovirus gag gene fused to a heterologous gene, or any part thereof, wherein the gag gene modification is sufficient to enable a cell to produce the hybrid gene product in a membraneous particle by budding from the cell membrane into the culture medium or extracellular space, a process known as retrovirus-mediated secretion. The modified gag gene may comprise the minimal regions of Gag that drive particle formation and budding, preferably at least amino acids 1–8, 84–174 and 417–515.

Optionally, the hybrid gene contains a proteolytic cleavage site joining the modified gag gene and the heterologous gene. Further, the hybrid gene is operably linked to one or more nucleotide sequences capable of directing expression of the hybrid gene product.

In one preferred embodiment an avian retrovirus gag gene is modified to encode a myristic acid addition site and to encode at least the minimal regions (or domains) of the gag gene sufficient to enable a mammalian or an avian cell to produce the gene product, or hybrid gene product when fused to a heterologous gene, in a membraneous particle.

Another aspect of this invention is directed to the hosts containing the instant expression vectors.

Yet another aspect of the present invention provides the hybrid gene product optionally having a genetically engineered proteolytic cleavage site of a retrovirus gag gene or other protease fused to a heterologous gene. Further, the present invention contemplates any cleavage products or fragments of the hybrid gene product.

Still another aspect of the instant invention is directed to the membraneous particles containing the hybrid gene products of the present expression vectors. These particles are useful for purifications of the hybrid gene products or fusion proteins as vaccines, as immunogens and as drug delivery systems.

A further aspect of the present invention provides a method of producing fusion proteins or membraneous particles by the process of retrovirus-mediated secretion.

DETAILED DESCRIPTION OF THE INVENTION

Figure 1:
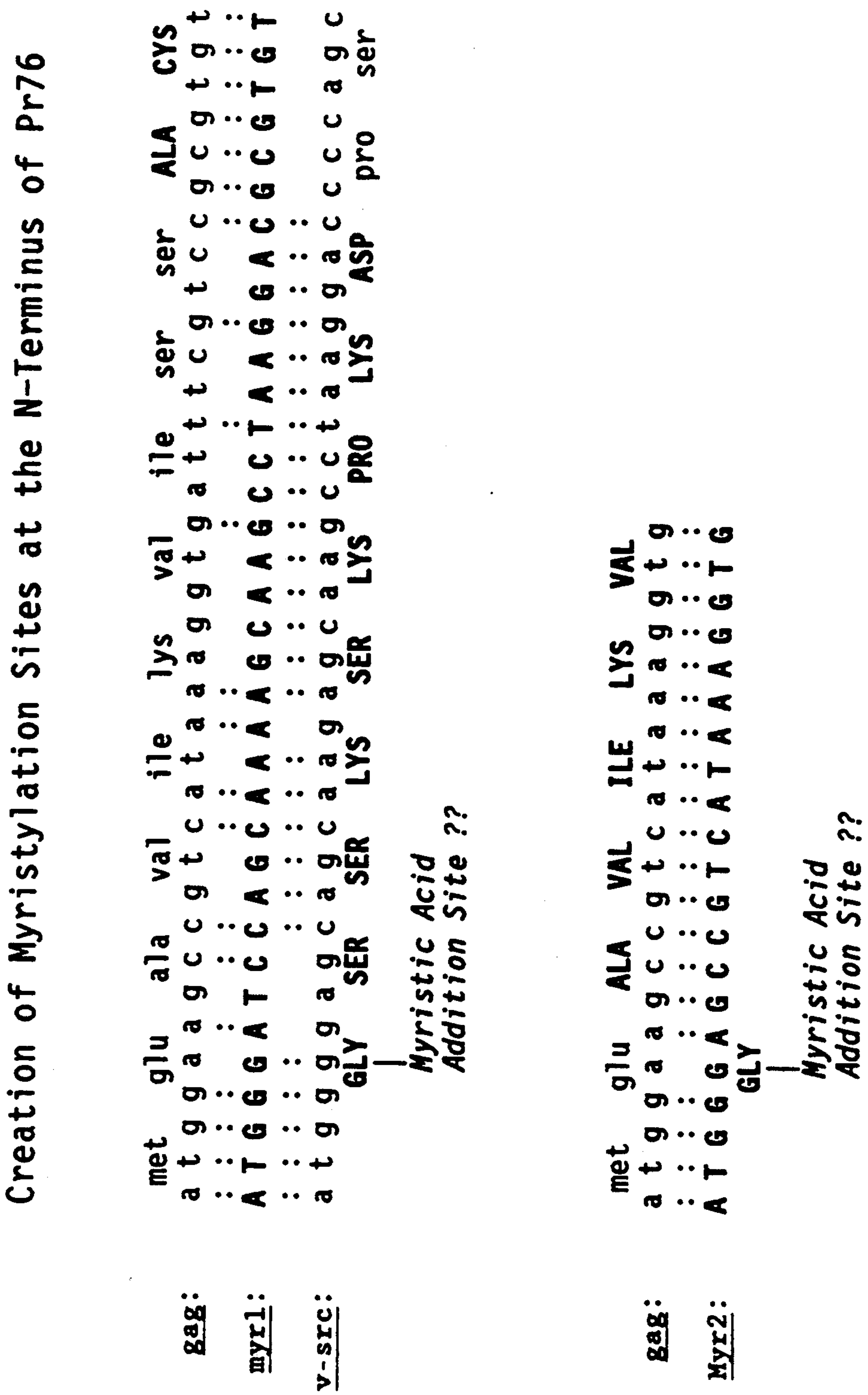
FIG. 1 depicts the 5'-end of RSV gag gene and the mutagenic oligonucleotides used to construct a myristylation site on $Pr76^{gag}$.

The present invention is directed to replicable expression vectors having one or more nucleotide sequences operably linked to a hybrid gene which is a fusion of at least part of a retrovirus gag gene and a heterologous gene, or a part, of the heterologous gene wherein said gag gene enables a cell to produce and release the hybrid gene product in a membraneous particle. Optionally, the hybrid gene contains a nucleotide sequence encoding a proteolytic cleavage site, which links the gag and heterologous genes. The present gag gene may be from an avian or mammalian retrovirus, and preferably is from an avian retrovirus.

The process for producing membraneous particles is known as retrovirus-mediated secretion. In cultured cells for example, it occurs by budding of the particle from the plasma or cell membrane. The budding process is akin to the production of infectious virus particles as well as immature virion particles.

Replicable expression vectors are generally DNA molecules engineered for controlled expression of a desired gene, especially high level expression were it is desirable to produce large quantities of a particular gene product, or polypeptide. The vectors comprise one or more nucleotide sequences operably linked to a gene to control expression of that gene, the gene being expressed, and an origin of replication which is operable in the contemplated host. Preferably the vector encodes a selectable marker, for example, antibiotic resistance. Replicable expression vectors can be plasmids, bacteriophages, cosmids and viruses. Any expression vector comprising RNA is also contemplated.

Preferred vectors are derived from eukaryotic sources. Expression vectors that function in tissue culture cells are especially useful, but yeast vectors are also contemplated. These vectors include yeast plasmids and minichromosomes, retrovirus vectors, BPV (bovine papilloma virus) vectors, baculovirus vectors, SV40 based vectors and other vital vectors. SV40-based vectors and retrovirus vectors (e.g., murine leukemia viral vectors) are preferred. Tissue culture cells that are used with eukaryotic replicable expression vectors include CV-1 cells, COS-1 cells, NIH3T3 cells, mouse L cells, HeLa cells turkey embryo fibroblast cells and such other cultured cell lines known to one skilled in the art.

Prokaryotic vectors that may also be suitable for expression of a hybrid gene of the instant invention include bacterial and bacteriophage vectors that can transform such hosts as *E. coli*, *B. subtilis*, Streptomyces sps. and other microorganisms. Many of these vectors are based on pBR322 including Bluescript (commercially available from Stratagene) and are well known in the art. Bacteriophage vectors that are used in the invention include lambda and M13.

Heterologous genes contemplated by the present invention may encode the full amino acid sequence of a protein, or only such part as is desired to be expressed. These parts can be fragments or domains of the heterologous protein. Heterologous genes are linked to the gag gene by ligation of compatible restriction sites, by blunt-end ligation or using appropriately designed oligonucleotide linkers. Preferred heterologous proteins for expression in this system include yeast cytochrome c (CYC1 gene), cytokines, lymphokines (interferons, interleukins, growth factors), therapeutic proteins, or any protein for which a gene sequence is available and for which production or rapid purification of that protein is desirable. Further, any protein useful as an inununogen, useful in a vaccine, or which needs to be targeted to a specific cell for therapeutic purposes, i.e., a drug delivery system, can also be expressed in this system. If a gene sequence is not available, then it can be determined from the protein's amino acid sequences and chemically synthesized by standard DNA synthesis techniques. Further, the invention contemplates any modifications or mutation of a protein being expressed by the present expression vectors.

The optional proteolytic cleavage site of the present invention is located between the Gag domain and the heterologous domain in the fusion protein, i.e. at the point of fusion. A proteolytic cleavage site can be introduced when later separation of these two domains is desired. The proteolytic cleavage site comprises amino acid residues recognized and enzymatically cleaved by a protease. Any known protease cleavage site is contemplated by the present invention, including the sites recognized by retroviral proteases, collagenase, Factor VIII and Factor IX.

Sequence elements capable of effecting expression of a gene include promoters, enhancer elements, transcription termination signals and polyadenylation sites. The latter three elements are not always necessary and their use will depend on both the vector and host system used for gene expression. The need for any of these elements can be easily determined by one skilled in the art. Promoters are DNA sequence elements for controlling gene expression, in particular, they specify transcription initiation sites. Prokaryotic promoters that are useful include the lac promoter, the trp promoter, and $P_L$ and $P_R$ promoters of lambda and the T7 polymerase promoter. Eukaryotic promoters are especially useful in the invention and include promoters of vital origin, such as the SV40 later promoter and the Moloney Leukemia Virus LTR, yeast promoters and any promoters or variations of promoters designed to control gene expression, including genetically-engineered promoters. Control of gene expression includes the ability to regulate a gene both positively and negatively (i.e., turning gene expression on or off) to obtain the desired level of expression.

One skilled in the art has available many choices of replicable expression vectors, compatible hosts and well-known methods for making and using the vectors. Recombinant DNA methods are found in any of the myriad of standard laboratory manuals on genetic engineering.

The replicable expression vectors of the present invention can be made by ligating part or all of a retrovirus gag gene to part or all of a heterologous gene to form a hybrid gene and then ligating the hybrid gene in the proper orientation to the promoter and other sequence elements being used to control gene expression. The gag gene region of the present invention is any portion or region of the gag gene sufficient to enable a cell to secrete the fusion product in a membraneous vesicle. For mammalian and arian retroviruses, removal of C-terminal residues or alteration (mutations), thereof in the Gag protein can allow processing and budding. However, it may be that some N-terminal residues can be deleted or changed and still enable the formation of membraneous particles. One skilled in the art can determine the maximum extent of a permissible deletion, at either the C-terminus or N-terminus, by constructing those deletions using standard genetic engineering techniques, such as deleting between convenient restriction enzyme sites; using Bal31 or ExoIII digestion for making deletions, or inserting protein termination codons into various sites and then assaying each construct for release of the genetically-engineered gag gene product into the culture medium in membraneous particles. Likewise, mutations in the gag gene, for example made by site-directed mutagenesis or natural selection can be assayed for gag-containing particles. To assay for the presence of the membraneous particles, the culture medium is removed from cells and subjected to high speed centrifugation to collect the particles. The particles are then analyzed for the presence of the Gag products by immunoprecipitating with anti-Gag antibodies.

For example, by constructing a variety of deletion derivatives in the gag gene encoding $Pr76^{Myr1}$ (described below), the regions of gag which are essential for membrane particle formation and budding have been identified. These derivatives, fully described in the examples and illustrated in FIG. 12, indicate that at least amino acids 1-8, 84-174 and 417-515 of $Pr76^{myr1}$ (the $myr_1$ allele) can to drive the budding process via a gag gene product adapted to enable a cell to secrete a fusion product in a membraneous particle.

However, further deletion derivatives can be made by deleting sequences between convenient restriction sites, inserting termination condons by oligonucleotide-directed mutagenesis or by Bal31 digestion to further delimit the region of the gag gene sufficient to enable formation of membrane particles and budding. These derivatives allow identification of smaller regions of the gag gene encoding only some of the amino acids defined above that are required for particle formation. Therefore, the present invention contemplates any part of a gag gene encoding a region, particularly from among contiguous sequences of amino acids 1-8, 84-174 and 417-514, which enables a cell to produce a hybrid gene product in a membraneous particle. Complementation-rescue of the deletion derivatives that are incapable of directing particle formation, indicate that the minimum essential region for particle formation may reside in the amino acid domain 417-515 of $Pr76^{Myr1}$.

In some instances, particularly with avian gag genes, and a few mammalian gag genes, it is necessary to introduce a modification into the gag gene to enable the Gag protein to direct formation of membraneous particles in the desired cell types. In the case of avian gag especially RSV gag, this modification involves altering the gene so that the protein is myristylated and, thus can bud in mammalian cells. Such a modification can be made, for example, by site-directed mutagenesis or oligonucleotide splicing of gene segments to form the desired modification.

The acyl group of myristylated proteins is added to an amino-terminal glycine which becomes exposed following the removal of the initiator methionine. There appears to be a requirement for glycine at residue 2. The importance of residues adjacent to Gly-2 for the recognition by N-myristyl transferase is not fully understood (Schultz et al.). Hence, many different mutations can be made provided residue 2 is glycine. Alternatively, the N-terminal residues of a protein known to be myristylated can be introduced onto the desired gag gene product by genetic engineering techniques. For RSV Pr76, two myristylation sites have been made. In one instance, the second RSV gag codon is changed from GAA (glutamic acid) to GGA (glycine). This creates the $myr_2$ allele of the RSV gag gene whose product is $Pr76^{myr2}$. This change can be accomplished by site-directed mutagenesis of a nucleic acid encoding the N-terminus of the RSV gag gene and using the mutagenic oligonucleotide:

5'-CAAGCATGGGAGCCGTCATAAAGG-3'.

In another instance, the first 10 amino acids of RSV $Pr76^{gag}$ are replaced by the first 10 amino acids of $p60^{v-src}$, a protein known to be myristylated. This creates the $myr_1$ allele of the RSV gag gene, whose product is $Pr76^{myr1}$. This change is accomplished in a manner similar to the construction of the $myr_2$ allele but using the mutagenic oligonucleotide:

5'CCCGGTGGATCAAGCATGGGATCCAG-CAAAAGCAAGCCTAAGGACGCGT-GTAAAACC-3'.

Any gag gene modification that encodes a myristic acid addition site is contemplated by the present invention.

Preferred replicable expression vectors of the present invention include for examples MGAG.$myr_o$, MGAG.-$myr_1$, MGAG.$myr_2$, pΔSV.GAGX, pΔSV.$Myr_x$, pΔSV.$Myr_o$, pΔSV.$Myr_1$, pΔSV.$Myr_{1A}$, pΔSV.$Myr_{1B}$, pΔSV.$Myr_{1C}$, pSV.$Myr_2$, pSV.MyCYE and pSV.MyCYC1. Preferred replicable expression vectors encoding the deletion derivatives of the present invention include pSV.Myr1.R-3K, pSV.Myrl.R-3A, pSV.Myrl.R-3C, pSV.Myrl.R-3J, pSV.Myrl.MA1, pSV.Myrl.Es-Bg, pSV Myrl.3h, pSV.Myrl.PR-Al*, pSV.Myrl.Sm-Bs, pSV.Myrl.DM1, pSV.Myrl.DM2, pSV.Myrl.TM and pDo.Myr1. The construction of these vectors is described in Example 2 and Example 11. The invention further contemplates any derivatives of these vectors which retain the properties of the instant invention. These derivatives can be made by genetic engineering techniques or obtained by natural selection.

The specific vectors described transiently produce fusion proteins by the retrovirus-mediated secretion path. The invention further contemplates vectors that lead to stable production of fusion proteins by the retrovirus-mediated secretion path.

Constitutive or stable expression of Pr76 fusion proteins can be accomplished using a gene transfer method based upon murine leukemia virus (MLV) expression vectors and other host systems. This method involves a helper cell line for packaging the recombinant MLV-RSV gag genome and an MLV-based transfer vector which expresses the recombinant MLV-RSV gag RNA. The RSV gag gene fusion is introduced into the transfer vector by standard recombinant techniques. Many such vectors are available and contain bacterial plasmid sequences and two MLV LTRs (Long Terminal Retreats). Between the LTRs are found the MLV packaging sequences (Ψ), the foreign gene of interest (i.e. the RSV gag gene fusions) and a selectable marker (e.g., a neomycin resistance gene under control of an appropriate promoter). The transfer vector is used to transfect a packaging cell line. This cell line releases infectious virion particles which contain RNA transcripts produced from the transfer plasmid. These virion particles are used to infect the target cells which will constitutively express and release RSV-Gag fusion proteins in membraneous particles.

A packaging cell line, for example GP+env AM12, is a cell line constructed using mouse 3T3 cells, which continuously expresses MLV Gag, Pol, and Env proteins. The cells release particles continuously, but the particles are not infectious because they do not package MLV RNA. There are two reasons for the packaging defect. First, the gag, pol, and env genes are present, but the sequences required for packaging the RNA genome (these are named Ψ) are not present on the gag, pol, and env transcripts. Second, the RNA is not packaged because the helper MLV genome has been "fragmented" and introduced into different sites in the 3T3 genome.

The env gene in this cell line is derived from an amphotropic strain of MLV having glycoproteins on the surface of its particles which have a very broad host range (mouse, human, canine, simian, etc.).

Infected target cells are identified via the selectable marker introduced by the transfer vector and then clonally expanded. MDCK (canine) and CV-1 cells are examples of two target cell lines that can be selected to express and release the non-infectious, membraneous particles containing the RSV gag fusion proteins. The particles are produced as a result of expression c,f the RSV gag fusion protein in the target cell, and especially myristylated RSV gag fusion proteins.

Another aspect Of the present invention provides a nucleic acid encoding a hybrid gene which can be used in constructing a replicahie expression vector of the present invention. The nucleic acid is composed of DNA or RNA. Further, the nucleic acid can be recombinant DNA or RNA. The hybrid gene encodes a hybrid gene product which is a fusion protein that is secreted by the retrovirus-mediated path into membraneous particles found in the extracellular space or culture medium.

Yet another aspect of the present invention provides transformant microorganisms and cultured cells containing the instant expression-vectors. Transformant microorganisms and cultured cells are made by introducing the replicable expression vector into the desired cell or microorganism by transformation or transfection, or infection of virus or bacteriophage particles. Processes for transformation are well known in the art and include but are not 3limited to $CaCl_2$ treatment and electroporation for bacterial cells and $CaPO_4$ coprecipitation, protoplast fusion and electroporation for eukaryotic cells. Direct infection can be used when the vectors are viruses or bacteriophages. The detailed methods for these techniques can be found in standard laboratory manuals on recombinant DNA technology. The invention further contemplates any method for incorporating DNA into a host organism.

Another aspect of the present invention provides a fusion protein having one domain which is a retrovirus Gag protein adapted to enable a cell to produce the fusion protein in a membraneous particle, i-e., by retrovirus-mediated secretion. The fusion protein has a second domain which is a heterologous or foreign protein. This second domain of the fusion protein consists of the entire foreign protein or any fragment or domain thereof desired to be expressed. A domain may be a region of a protein that forms a substructure of that protein. A domain may also specify a region having a specific enzymatic activity, a ligand binding site, a proteolytic cleavage site, or any other discrete feature of the protein. Further, the second domain can consist of any open reading frame encoded on a nucleic acid. Preferred proteins for fusion to the Gag domain include yeast cytochrome c, cytokines, lymphokines (interferons, interleukins), growth factors, therapeutic proteins or any other useful protein desired to be produced, and especially those proteins wherein rapid purification is desired or which can be used as an immunogen in a vaccine or in a drug delivery system. Any fragment or domain of these proteins can be fused to the Gag domain. Further, any modification, substitution, insertion or deletion in these proteins can be fused to the Gag domain.

Optionally, the fusion proteins can have a genetically engineered proteolytic cleavage site between the Gag domain and the second domain encoding the heterologous protein. The proteolytic cleavage site comprises a specific sequence of amino acid residues that are recognized and cleaved by a protease. Any known proteolytic cleavage site is contemplated by the present invention, including but not limited to the sites recognized by retrovital proteases collagenase, Factor VIII and Factor IX or even a retroviral protease.

In addition, the present invention contemplates any cleavage product or fragment of the above fusion proteins. These products may be produced by chemical means, produced by enzymatic means before or after isolation, especially by a protease, which recognizes a proteolytic cleavage site genetically engineered into the fusion protein, or produced during the course of retrovirus-mediated secretion by cellular proteases. In the latter instance, it is postulated that an unknown cellular protease may be responsible for the processing events. In any event, the processing events which occur during retrovirus-mediated secretion may generate fusion protein fragments contemplated by the present invention.

Still another aspect of the present invention provides membraneous particles of, produced by retrovirus-mediated secretion and containing any of the fusion proteins described above. Membraneous particles are membrane-enveloped pertinacious particles that are believed to resemble immature retrovirus particles. Their exact structure is not known. In the case of mammalian and arian cells, the membrane envelope components (i.e., phospholipids and proteins) are from the plasma membrane. The particles also include the fusion proteins described herein. The membraneous particles are useful for rapid protein purification, as immunogens, in vaccines and as drug delivery systems. In the latter case specific cells can be targeted for therapeutic treatment by varying the host cell used for retrovirus-mediated secretion so that the membrane of the particles contain specific receptors or ligands which will interact with the target cell. The membraneous particles also contain the "drug" being delivered to the target cell. In the case of retrovirus-mediated secretion, the "drug" is the fusion protein, or a domain or fragment of the fusion protein. Any protein domain useful in treating diseases may be fused to the Gag protein and produced as described herein.

The membraneous particles can be used as immunogens or in vaccine preparations. For example, the desired antigen (i.e., heterologous protein domain is fused to the Gag protein and expressed by retrovirus-mediated secretion as described herein. The membraneous particles are collected from the culture medium and purified by centrifugation. The membraneous particles are immunogenic and will elicit an immune response to the fusion protein. Hence, the particles may be incorporated into a vaccine composition or serve directly as the immunogen. Any heterologous protein, or domain thereof, useful in preparing antibodies, such as hepatitis B surface antigen, lymphokines or viral surface antigens may be fused to the Gag protein and thus yield the membraneous particles of the present invention.

Another aspect of the invention provides a method of producing a fusion protein a fragment thereof or a membraneous particle. The steps contemplated are as follows:

(a) transforming a cell with a replicable expression vector which contains a retrovirus gag gene, which is adapted to enable a cell to produce the fusion protein in a membraneous particle, fused to a heterologous gene or part thereof to form a hybrid gene operably linked to one or more nucleotide sequences capable of effecting expression of said hybrid gene;

(b) cultivating the cell for a time and under conditions sufficient to express said fusion protein in a membraneous particle; and (c) recovering said fusion protein or fragment from the membraneous particles or recovering the membraneous particles.

Accordingly, adaption of the retrovirus gag gene includes any modification, insertion, or deletion to the gene as described herein, such that upon expression of the fusion protein, the Gag domain will direct the fusion protein to be secreted by the cell in membraneous particles, i.e., by retrovirus-mediated secretion.

The following examples further illustrate the invention.

EXAMPLE 1

General Materials and Methods

DNA, Viruses, and Cells.

The wild-type RSV gag gene was obtained from PATV-8 (Katz et al. 1982, J. Virol. 42: 346–351), a molecule clone containing an infectious, sequenced copy of the RSV Prague C genome (Schwartz et al. 1983, Cell 32: 853–869). Plasmid PJD100 carries an infectious but unsequenced copy of the Prague A strain of RSV (Stoltzfus et al. 1987, J. Virol. 61: 3401–3409). RSV was grown in turkey cell cultures which were prepared from fertile eggs (Hudson Farms, Muskogee, Okla.) and propagated in supplemental F10 medium (primary growth medium, PGM) using previously published methods (Hunter, 1979, Meth. Enzymol. 58: 379–393). The turkey cell cultures were found to contain no sequences capable of recombining with RSV gag sequences and produced no RSV specific antigens. Prague A(JD100) and Prague C(ATV-8) virus was obtained by transfecting secondary turkey cell cultures with pJD100 or pATV-8 DNA, respectively. Recombinant plasmids were propagated in *E. coli* strain DH-1 using solid or liquid LB medium containing 25 μg of ampicillin per ml. Recombinant M13 phages were propagaged in LB medium without ampicillin. The SV40 vector used for the expression of wild-type and mutant RSV gag genes in mammalian cells was derived from a previously described construction (Wills et al. 1984, J. Cell Biol. 99: 2011–2023) as explained in Example 2. African green monkey kidney cells (CV-1) or COS-1 cells, used for the transfection of SV40-gag DNAs, were propagated in Dulbecco's modified medium supplemented with 3% fetal bovine serum and 7% adult bovine serum (Hyclone, Inc.).

Recombinant DNA methods for restriction enzyme digestions, ligations, and various other enzymes (DNA polymerase Klenow fragment, Mung bean nuclease, etc.) were used according to manufacturer's recommendations.

Transfection of mammalian cells.

Prior to transfection, the SV40-gag DNAs were digested with XbaI to remove the bacterial plasmid sequence (see FIG. 2) and then ligated at low DNA concentrations to connect the 3'-end of the gag gene with the late SV40 polyadenylation signal. CV-1 cells were transfected using a variation of the DEAE-dextran and chloroquine method previously described (Wills et al., 1984). Briefly, 60 mm plates containing 90–95% confluent monolayers were washed twice with PBS (phosphate-buffered saline) and twice with TBS (Tris-buffered saline) immediately before adding 500 μl of the DNA mixtures (TBS containing 1–2 μg of ligated DNA and 0.5 mg DEAE-dextran). After incubation at 37° C. in a $Co_2$ incubator for 45–60 min, the DNA was removed from the monolayers and replaced with regular CV-1 growth medium containing 100 μM chloroquine for 4 h. The latter step enhances the delivery of the transfected DNA to the nucleus (Luthman et al. 1983, Nucleic Acids Res. 11: 1295–1308), appears important for high levels of gag expression. After chloroquine treatment, the monolayers were returned to normal CV-1 growth medium.

Transfection of arian cells.

Turkey cells were transfected in 60 mm plates (80–90% confluent) using the above described DEAE-dextran method except that only 100 μg of DEAE-dextran was used per 500 μl of DNA in TBS, and the cells were incubated in serum-free medium, instead of medium with chloroquine, for 4 h before returning to normal growth medium. Cells transfected with infectious RSV DNA using this procedure exhibit complete morphological transformation after 3–4 days.

Metabolic labeling of transfected cells.

CV-1 or COS-1 cells were labeled with radioisotopes 48 h after transfection, and transfected turkey cells were labeled after the monolayers had become completely transformed. For labeling with L-[$^{35}$S]methionine(1000 Ci/mmol, ICN Biomedicals), the cells were washed once with PBS and then 800 μl of methionine-free, serum-free median containing 50 μCi of $^{35}$S-methionine, was added. After 30 min of labeling, cold methionine was added to a final concentration of one tenth the amount found in normal Dulbecco's medium, and the labeling was continued for 2 h.

Transfected CV-1 cells were labeled with [9,10(n)-$^{3}$H]-myristic acid (47.5 Ci/mmol, Amersham International) following the general method of Rhee et al. $^{3}$H-myristic acid was dried under a gentle stream of nitrogen to evaporate the toluene solvent and dissolved in dimethyl sulfoxide (DMSO) at a concentration of 30 μCi/μl. The isotope was then added to complete CV-1 growth medium to give a final concentration of 1 mCi/ml. Each 60 mm plate was labeled with 400 μl (0.4 mCi) of this medium for 1 h at 37° C.

Fractionation of cell cultures.

After labeling, the medium from each plate (800 μl ) was removed and mixed with 200 μl of 5× lysis buffer B (125 mM Tris hydrochloride [pH 8.0], 0.75M NaCl. 0.5% SDS, 5% Triton X-100, 5% deoxycholate) containing 5× protease inhibitors (500 μg/ml phenylmethyl-sulfonyl fluoride, 5 μg/ml pepstatin, 5 μg/ml leupeptin). Monolayers were lysed using 500 μl of 1× lysis buffer A (25 mM Tris hydrochloride [pH 8.0], 0.15M NaCl, 1% Triton X-100, 1% deoxycholate) containing 1× concentrations of protease inhibitors. The plates were washed again with 500 μl of lysis buffer A, and nuclei were removed from the 1 ml lysate by centrifugation at 15,000 g for 1 min. The supernatant was transferred to a clean tube and mixed with 10 μl of 10% SDS.

Immunoprecipitation of gag proteins.

500 μl samples were incubated with an excess of anti-serum at 4° C. for 12–16 h. For most of the experiments, rabbit anti-p27 serum was used. This antiserum primarily recognized the RSV capsid protein and processing intermediates that contain p27, but it also has low reactivity with other RSV gag products. To better collect other gag products, goat antiserum against whole RSV (Microbiological Associates, Inc.) was used followed by a 2 h incubation with rabbit serum against goat IgG (Cappel Laboratories). In other experiments anti-RSV Gag and anti-Gag peptide antibodies which were generated by standard techniques (e.g. Harlowe et al. 1988, Antibodies: A Laboratory Manual, Cold Spring Harbor Laboratory Press, N.Y.) were employed. All antigen-antibody complexes were collected with fixed *S. aureus* using standard procedures (Harlow et al. supra). The complexes were washed twice with 1× lysis buffer B, once with 20 mM Tris hydrochloride (pH 8.0) and then disassociated in 20 μl of sample buffer (60 mM Tris hydrochloride [pH 6.8], 10% glycerol, 2% SDS, 2% β-mercaptoethanol, 0.001% bromophenol blue) by heating at 90° C. for 1–2 min. Immediately prior to electrophoresis, the free *S. aureus* cells were removed by centrifugation.

SDS-polyacrylamide gel electrophoresis.

Immunoprecipitated proteins were electrophoresed in 1.5 mm thick SDS-polyacrylamide gels using standard methods (Harlow et al. Supra). Resolving gels and stacking gels were prepared using a 29:1 ratio of acrylamide monomer and cross-linker (N,N'-methylene-bis-acrylamide). The resolving portion of the gels contained acrylamide (7%, 10%, or 15% as noted), 0.1% SDS, and 400 mM Tris Hydrochloride (pH 8.8). The stacking gels contained 3% acrylamide, 0.1% SDS, and 60 mM Tris hydrochloride (pH 6.8). After electrophoresis, the separated proteins were fixed and stained with Coomassie blue R250 (0.003% Coomassie blue in 10% acetic acid—50% ethanol). Subsequently, the gels were destained in a solution of 5% methanol, 7% acetic acid. The radioactive bands were detected by fluorography using Fluoro-Hance (Research Products International, Inc.) and Kodak X-OMAT AR5 film at −70° C. Typically, exposures of 1–16 h were required for the detection of $^{35}$S-methionine labeled proteins while $^{3}$H-myristic acid labeled proteins required exposures of 1–2 weeks.

EXAMPLE 2

Mutagenesis and Plasmid Constructions

A. Oligonucleotide-directed mutagenesis.

The coding sequence for the RSV gag gene lies between nucleotides (nt) 380 and 2482 in the RSV genome (Schwartz et al.). The SacI-HindIII fragment containing this region (nt 225 to 2740, respectively) was cloned into the polylinker region of M13mp19. The resulting clone is named MGAG. Mutagenesis of MGAG was accomplished using the method Kunkel (Kunkel et al. 1987, Meth. Enzymol. 154: 367–382). MGAG phage was sequentially propagated three times in CJ236, a dut ung strain of *E. coli,* in order to replace thymine with saturating amounts of uracil. Single-stranded DNA was then isolated for use as the template for mutagenesis. Mutagenic oligonucleotides were synthesized using an Applied Biosystems DNA synthesizer, gel purified, phosphorylated using T4 polynucleotide kinase, hybridized with the uracil-containing template, made double-stranded using T4 DNA polymerase, and sealed using T4 DNA ligase. The products of these reactions were transfected into a Dut+Unq+ strain and plated to allow selection and segregation of the mutants. The resulting plaques were picked and the phages were grown to obtain RF DNA and ssDNA. Clones containing the desired mutations were identified by DNA sequencing use of the method of Sanger (Sanger et al. 1977. Proc. Natl. Acad. Sci. USA. 74: 5463–5467).

The clone MGAG.$myr_0$ is MGAG that was not mutagenized.

The clone MGAG.$myr_1$ was made by substituting the first 10 codons of gag for those of RSV src. A 57-mer was used (5'CCCGGTGGATCAAGCATGGGATC-CAGCAAAAGCAAGCCTAAGGACGCGT-GTAAAACC-3') which was designed to maximize complementary (FIG. 1). As this change is rather complex, presumptive clones were initially identified by the presence of a newly introduced MluI site (ACGCGT) contained in the 57-mer. The resulting allele, confirmed by DNA sequencing, is designated $myr_1$.

The clone MGAG.$myr_2$ was made by changing the second codon of gag to code for Gly by introducing a single point mutation of A to G (FIG. 1). This was accomplished using a 24-mer (5'-CAAGCATG-GGAGCCGTCATAAAGG-3'), and the resulting allele is designated $myr_2$. Fragments containing the gag mutations were excised from the RF DNAs by digestion with SacI and BglII (nt 1630) for transfer to the mammalian expression vector.

B. Construction of the SV40-gag expression vectors.

Figure 2:
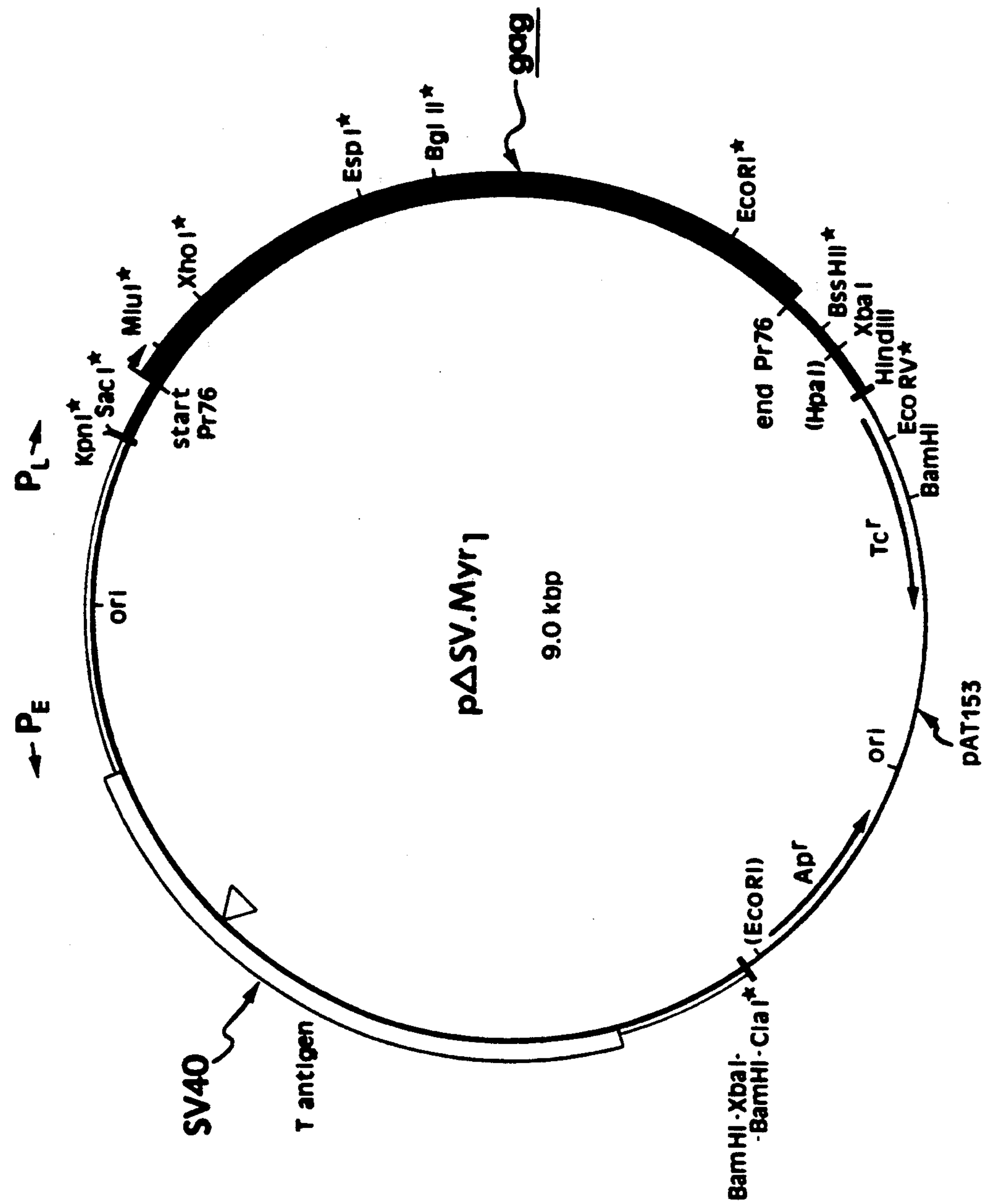
FIG. 2 depicts a restriction map of the expression vector p SV.$Myr_1$.

The wild-type ($myr_0$) and mutant ($myr_1$ and $myr_2$) gag genes were transferred to an SV40-based vector called pΔSV.$Myr_x$. In this vector, transcription is driven from the SV40 late promoter. The parent of pΔSV.$Myr_x$ is pΔSV.GAGX which expresses a truncated Gag protein whose amino-terminus is missing due to the presence of an out-of-free, upstream initiation codon in the SV40 sequence. A description of these two vectors follows.

i) pΔSV.GAGX. This plasmid contains DNA fragments from three sources: the RSV genome, the SV40 genome, and the bacterial plasmid, pAT153. The RSV Sac-HindIII fragments contains the gag gene and was modified by inserting an XbaI linker (5'-CTCTAGAG-3') into the HpaI site (nt2731) by means of blunt-end ligation. The SacI end was made blunt using the Klenow fragment of *E. coli* DNA polymerase. The HindIII end was not modified. The SV40 fragment was obtained from d12005, an SV40 mutant lacking approximately 230 bp of the T-antigen intron (Sleigh et al. 1978, Cell 14: 79–88). This viable mutant produces fully functional T-antigen. The fragment used here extends from the BamHI site (wild-type SV40 nt 2533) to the HpaII site (nt346) and includes the early region, replication origin, and late promoter; the portion of the SV40 genome which codes for capsid proteins is missing. The HpaII end was made blunt using Klenow and a ClaI linker was attached using T4 DNA polymerase. The BamHI end was modified with a polylinker resulting in the sequence of sites: BamHI-XbaI-BamHI-ClaI. The portion of pAT153 used lacks the 6 bp region between the ClaI and HindIII sites; the EcoRI site was removed by digestion with EcoRI, filling with Klenow, and ligating. Several subcloning steps were required to assemble p SV.GAGX and the final product is linked as follows: The destroyed HpaII end near the SV40 late promoter is joined to the destroyed SacI end of the RSV fragment by means of the ClaI linker. The 3'-end of the RSV fragment is joined to pAT153 via their intact HindIII sites. The intact ClaI end of the pAT153 sequence is joined to SV40 fragment via the ClaI site of the polylinker, BamHI-XbaI-BamHI-ClaI.

ii) pΔSV.$Myr_x$. Because the RSV SacI site was destroyed during the construction of pΔSV.GAGX, a new SacI site was inserted adjacent to the SV40 late promoter to permit the transfer of $myr_0$, $myr_1$ or myr2 into the expression vector. For this purpose, PΔSV.$Myr_x$ was created by digesting pΔSV.GAGX with Asp718I (a KpnI isoschizomer), making the ends blunt using Klenow, and then ligating a SacI linker (5'-CGAGCTCG-3'). This manipulation did not destroy the ASp7181 site.

iii) pΔSV.$Myr_0$, pΔSV.$Myr_1$, pΔSV.$Myr_2$. Digestion of PΔSV.$Myr_x$ with SacI and BglII removed the 5'-end of the gag gene as well as the upstream, out-of-frame SV40 initiation codon, but has no effect on the SV40 late promoter. Hence, replacement of the SacI-BglI fragment on p SV.$Myr_x$ with the same fragment from MGAG.$myr_0$, MGAG.-$Myr_1$, or MGAG.$myr_2$ created pΔSV-$Myr_0$, pΔSV.$Myr_1$ and pΔSV.$Myr_2$, respectively. The restriction map of pΔSV.$Myr_1$ is illustrated in FIG. 2.

iv) Truncated derivatives of pΔSV.$Myr_1$. Derivatives of pΔSV.$Myr_1$ were constructed by deleting restriction fragments at the 3'-end of the gag gene. Deletion of EcoRI-BssHII, BglII-BssHII, and EspII-BssHII fragments yielded vectors pΔSV.$Myr_{1A}$ and pΔSV $Myr_{1B}$ and pΔSV.$Myr_{1C}$ respectively. The deletions were made by digesting pΔSV.$Myr_1$ with the appropriate restriction enzyme, creating blunt ends by filling with Klenow and self-ligating the plasmid. The corresponding myr alleles are known as $myr_{1A}$, $myr_{1B}$ and $myr_{1C}$, respectively.

v) Deletion derivatives of pΔSV.$Myr_1$.

Figure 12:
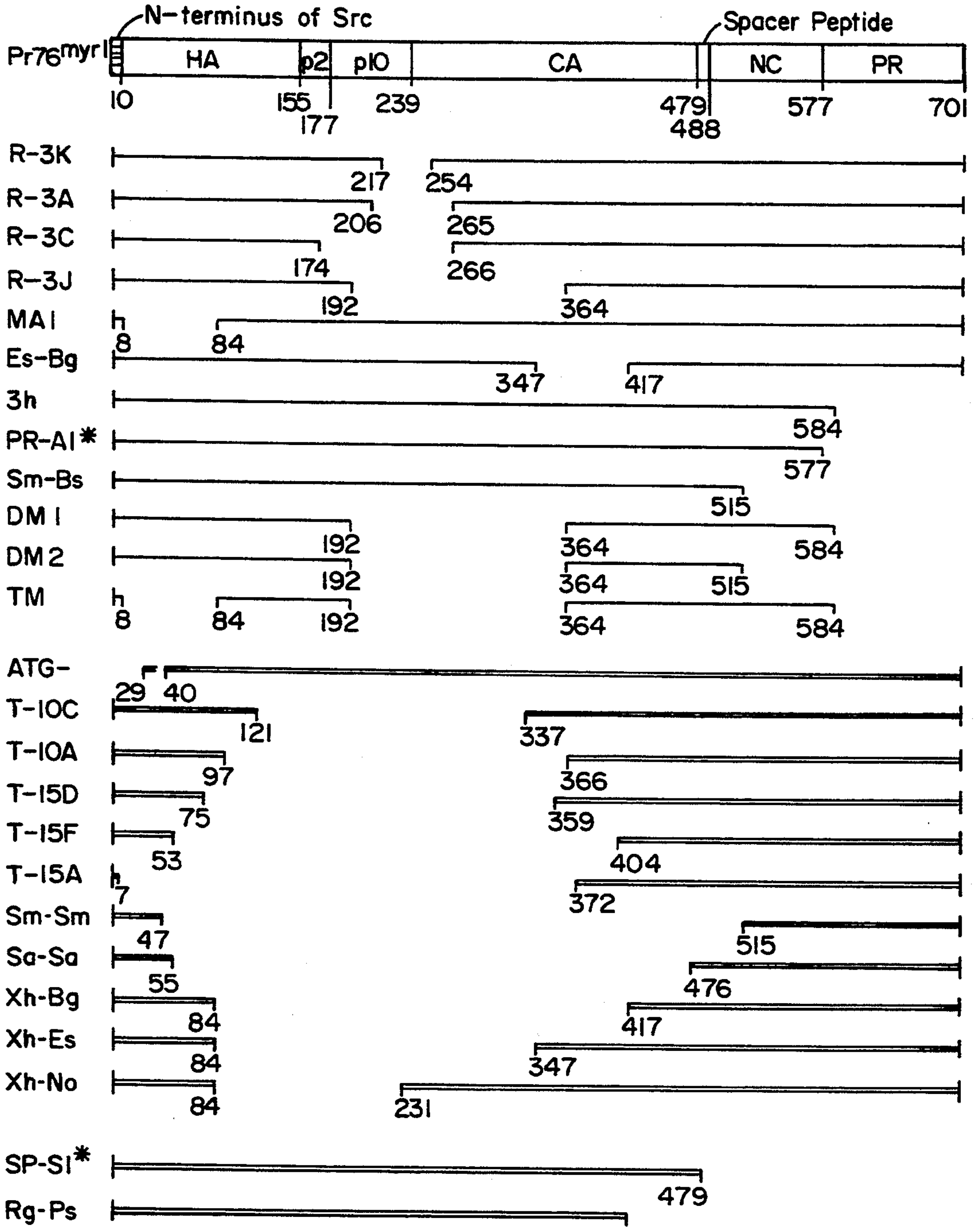
FIG. 12 is a schematic diagram illustrating the overall structure of $Pr76^{myr1}$ (top line) and a series of deletion derivatives of $Pr76^{myr1}$ (remainder of figure), which were used to establish which gag sequences are required for membrane particle formation. The derivatives were constructed in p SV.$Myr_1$, and the designations on the left represent the abbreviated names of the constructs, which are named pSV Myr1.Y where Y is the abbreviated name, for example, R-3K represents the construct pSV Myr1.R-3K, etc. The solid lines (upper, R-3K to TM) represent deletion derivatives that efficiently formed membrane particles; the open lines (lower, ATG- to Bg-Bs) represent deletion derivatives that did not form membrane particles efficiently. The shaded grey areas summarize the minimum gag residues needed to obtain efficient membrane particle formation and budding. Each line represents the regions of $Pr76^{Myr1}$ present in a given construct; the gaps indicate the deleted regions and the numbers indicate the amino acids of $Pr76^{Myr1}$ at the ends of the deletions. The (*) indicates that a stop codon was introduced at the indicated site in the polyprotein.

Deletions were made in $myr_1$ to identify the gag sequences required for membrane particle formation and budding. All derivatives were constructed in pΔSV.$Myr_1$ and the constructs were sequenced (in whole or in part) to insure that the desired deletion had been constructed, or in the case of the Bal-31 deletions, to determine the extent of deletion. FIG. 12 graphically depicts all the constructs and indicates the end points of each deletion (by amino acid residue). The system of nomenclature for these constructs is described in the description of FIG. 12 (supra). The corresponding alleles are defined as $myr_1$.Y where Y is the abbreviated construct name from FIG. 12.

For one set of deletions, a NotI site was introduced via a linker into pΔSV.$Myr_1$ at nucleotide 1070 (just before the CA coding sequence). The resulting plasmid was digested with NotI and treated with Bal-31 to generate the following constructs: pSV.Myr1.R-3K, pSV.Myr1.R-3A, pSV.Myr1.R-3C, pSV.Myr1.R-3J, pSV-Myr1.T-10C, pSV-Myr1.T-10A, pSV-Myr1.T-15D, pSV-Myr1.T-15F, and pSV.Myr1.T-15A.

To construct the deletion derivative pSV.Myr1.3h, pΔSV.$Myr_1$ was digested with EcoRV and then treated with Bal-31 to remove sequences downstream of the $myr_1$ allele.

Another series of deletion derivatives was generated by excising convenient restriction fragments from pΔSV.$Myr_1$. The general strategy involved digesting the plasmid with the desired, restriction enzyme, treating with Klenow to make blunt ends if non-compatible sticky ends were generated by enzymatic digestion, and then religating the plasmid. Specifically, pSV.Myr1-.MA1 was made by excision of a SauI-XhoI fragment; pSV.Myrl.Es-Bg was made by excision of a EspI-BglI fragment; pSV.Myrl.Sm-Bs was made by excision of a SmaI-BssHII fragment; pSV-Myrl. Sm-Sm was made by excision of a SmaI-SmaI fragment; pSV.Myrl. Sa-Sa was made by excision of the SacII-SacII fragment; pSV-Myrl.Xh-No was made by excision of a XhoI-NotI fragment; pSV-Myr1.Xh-Es was made by excision of a XhoI-EspI fragment; and pSV.Myr1.Bg-Bs was made by excision of a BglII-BssHII fragment.

Two deletion-type derivatives were constructed by inserting stop codons by oligonucleotide-directed mutagenesis. pSV-Myr1.PR-A1* introduced a stop codon for alanine (A) at the first residue of the PR coding sequence; pSV.Myr1.SP-S1* introduced a stop codon for serine (S) at the beginning of the spacer peptide immediately following the CA coding sequence.

Multi-deletion derivatives were generated by combining selected single deletion derivatives. pSV.Myrl.DMl was made by combining the deletions of the R-3J and 3h constructs. This was accomplished by inserting the SacI-BglII fragment of pSV.Myrl.R-3J (containing one deletion) into the same site on pSV.Myrl.3h. pSV.Myr1.DM2 was constructed by combining the deletions of the R-3J and Sm-Bs constructs. This was accomplished by inserting the SacI-BglII fragment of pSV-Myr1.R-3J (containing one deletion) into the same site on pSV.Myr1.Sm-Bs. Finally, pSV.Myr1.TM was constructed by combining the deletions of the DM1 and MA1 constructs. This was accomplished by removing the SauI-XhoI fragment from pSV-Myr1.DM1.

vi) Derivatives of pΔSV.$Myr_1$ with gag-cycl gene fusions.

Two plasmids were made which fused gag sequences from PΔSV.$Myr_1$ with sequences derived from the yeast iso-1-cytochrome c gene, CYC1. The plasmid pΔSV.MyCYE had the gag and CYC1 sequences joined out-of-frame. To make this plasmid, pΔSV.$Myr_1$ was sequentially digested with BssHII, treated with Mung bean nuclease and digested with EcoRI. In parallel, plasmid pAB16, carrying CYC1 (Smith, M. et al. 1979, Cell 16: 753–561) was sequentially digested with HindIII, treated with Mung bean nuclease and digested with EcoRI. The small EcoRI-HindIII fragment pAB16 was ligated to the large EcoRI-BssHII fragment of pΔSV.$Myr_1$ to generate pSV.MyCYE.

To create an in-frame fusion of gag and cycl sequences, pSV.MyCYE was digested with EcoRI, treated with Mung bean nuclease and religated under conditions favoring self-ligation thereby yielding plasmid pSV.MyCYC1.

The corresponding alleles from pSV.MyCYE and pSV.MyCYC1 are known as $myr_1$-cye and $myr_1$-cycl, respectively.

EXAMPLE 3

Myristylation of Modified RSV gag Genes Expressed in Mammalian Cells

To determine if $myr_1$ or $myr_2$ encode myristylated products, duplicate plates of CV-1 cells were transfected with either no DNA, pΔSV.$Myr_0$ (wild-type), pΔSV.$Myr_1$, or pΔSV.$Myr_2$ DNA. After 48 h, one plate of each pair was labeled with $^{35}$S-methionine (to determine the relative levels of gag expression) or with $^{3}$H-myristic acid for 1 h. After labeling, the medium was discarded, the cells were lysed, and nuclei were removed by centrifugation. The gag products were collected from the lysates by immunoprecipitation using an anti-p27 antibody, separated by SDS-polyacrylamide electrophoresis in a 10% gel, and visualized by fluorography.

When using $^{3}$H-myristic acid, lengthy labeling periods were avoided; otherwise, the labeled molecules would be metabolized by the cells, and the tritium incorporated into non-myristylated proteins. The conditions used here avoided that problem, since labeling of the wild-type, $Pr76^{myr0}$, was not observed (FIG. 3B, lane 2). Identical results were obtained with periods of up to 2 h; however, trace amounts of 3H-labeled proteins that are known not to be myristylated can be seen after 2.5. h.

Figure 3A:
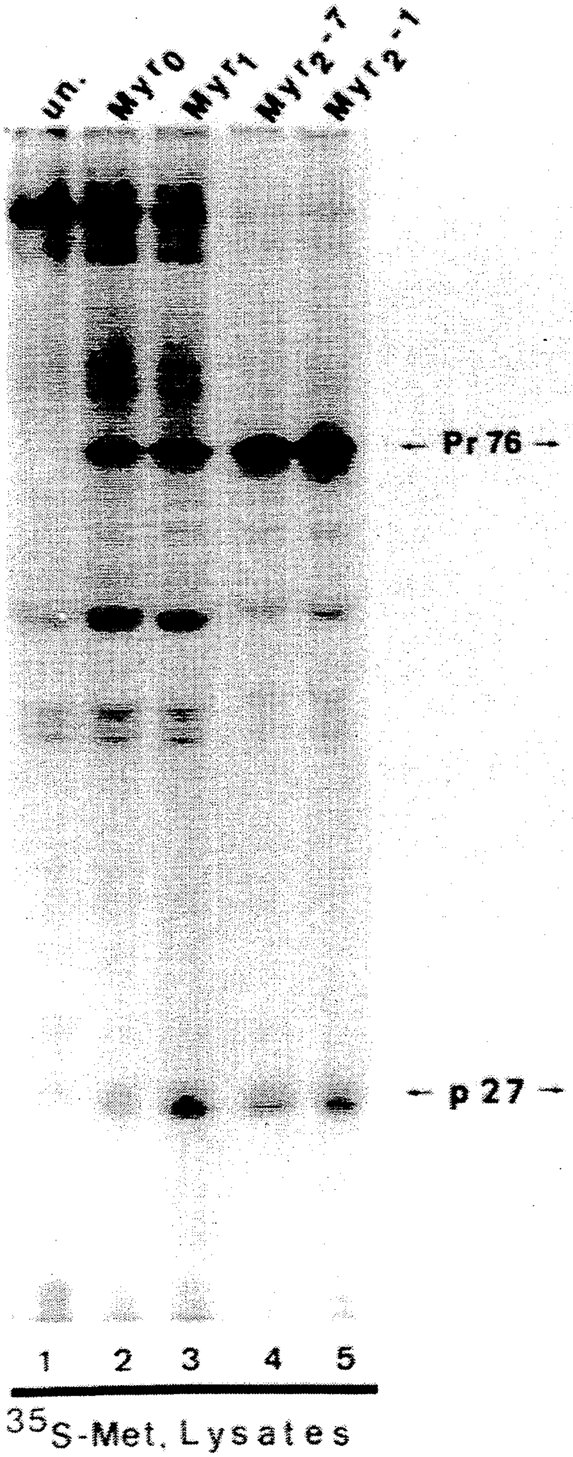
FIGS. 3A and B represent an autoradiograph illustrating that a modified avian Gag protein ($Pr76^{myr1}$ and $Pr76^{myr2}$) is myristylated in mammalian cells.
Figure 3B:
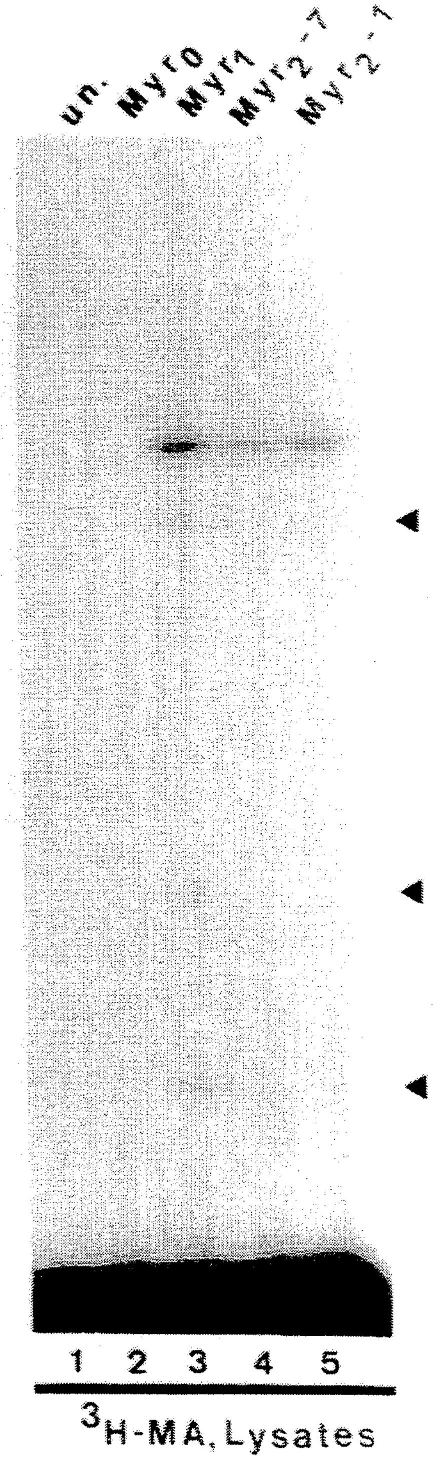

It is clear from the $^{35}$S-methionine results shown in FIG. 3A {(lanes 2–5), that each of the SV40-gag DNAs expressed a full length product (Pr76) (lanes 2–5) while untransfected cells (lane 1) showed only nonspecific background bands. The differences in intensity between $Pr76^{myr0}$ (lane 2), $Pr76^{myr1}$ (lane 3) and the two clones of $Pr76^{myr2}$ (lanes 4 and 5) reflect differences in the amount of DNA used in this particular experiment. Results from many other experiments have shown that the DNAs that encode these proteins have equal expression potential. Labeling with $^{3}$H-myristic acid demonstrated that both $Pr76^{myr1}$ and $Pr76^{myr2}$ are myristylated (FIG. 3B, same lane designations as FIG. 3A) (panel B). A comparison of the relative band intensities obtained with $^{35}$S-methionine and $^{3}$H-myristic acid suggests that the myristic acid addition site on $Pr76^{myr2}$ is less frequently used than that of $Pr76^{myr1}$. Also apparent are bands that probably represent proteolytic processing intermediates (FIG. 3B, arrowheads). Those detected with the $^{3}$H-myristic acid label presumably represent intermediates that contain the amino-terminal portion of Pr76. (The broad band present at the bottom of all the lanes is due to the binding of unincorporated but hydrophobic $^{3}$H-myristic acid to *S. aureus*.)

EXAMPLE 4

Myristylated RSV gag Proteins Produced in Mammalian Cells Are Released into the Medium To further characterize the abilities of the various forms of Pr76 to be processed and released by budding, transfected CV-1 cells were labeled for 2.5 h with $^{35}$S-methionine, and the culture medium and the cell lysates were analyzed using antibodies against p27 or against RSV gag proteins. Turkey cells infected with Rous sarcoma virus were labeled to obtain authentic gag products for comparison and to show the antibody specificity. Preliminary experiments revealed intracellular half-lives on the order of 30 min for all forms of Pt76; thus, the results obtained using a 2.5 h labeling period approximate steady-state conditions.

Figure 4A:
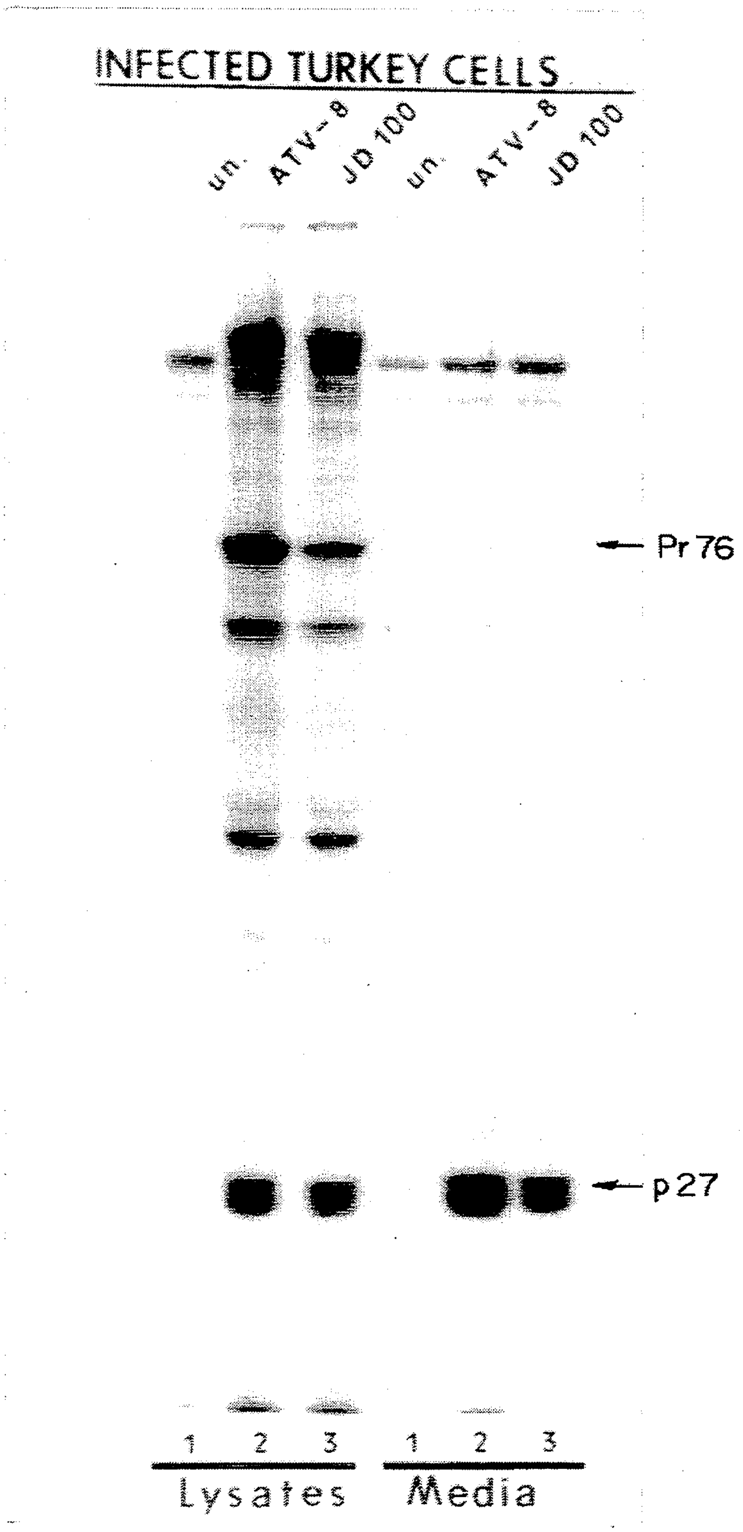
FIGS. 4A and B represent an autoradiograph illustrating that a myristylated RSV Gag protein ($Pr76^{myr1}$) is secreted into the culture medium and is processed like wild-type RSV Pr76.

For the RSV control experiment, two molecularly cloned RSV strains were used: JD100 (Prague A) and ATV-8 (Prague C). Both gave identical profiles of radiolabelled proteins on the fluorogram (FIG. 4A). (The uppermost band seen even in the uninfected control is fibronectin which binds to *S. aureus* cells during the immunoprecipitation.) In the lysates, the most conspicuous bands are Pr76$^{gag}$ (arrow), two processing intermediates of approximately 60 kDa and 47 kDa, and a characteristic doublet of bands running at the expected position of p27 (arrow). These five bands are observed with these two widely used infectious clones. The "p27-doublet" represents mature products, since it is also seen in the medium samples whereas the three larger polypeptides are not. The lack of a significant amount of processing intermediates in the medium was confirmed by pulse-chase experiments and indicated the efficiency of cleavage during the budding process.

Figure 4B:
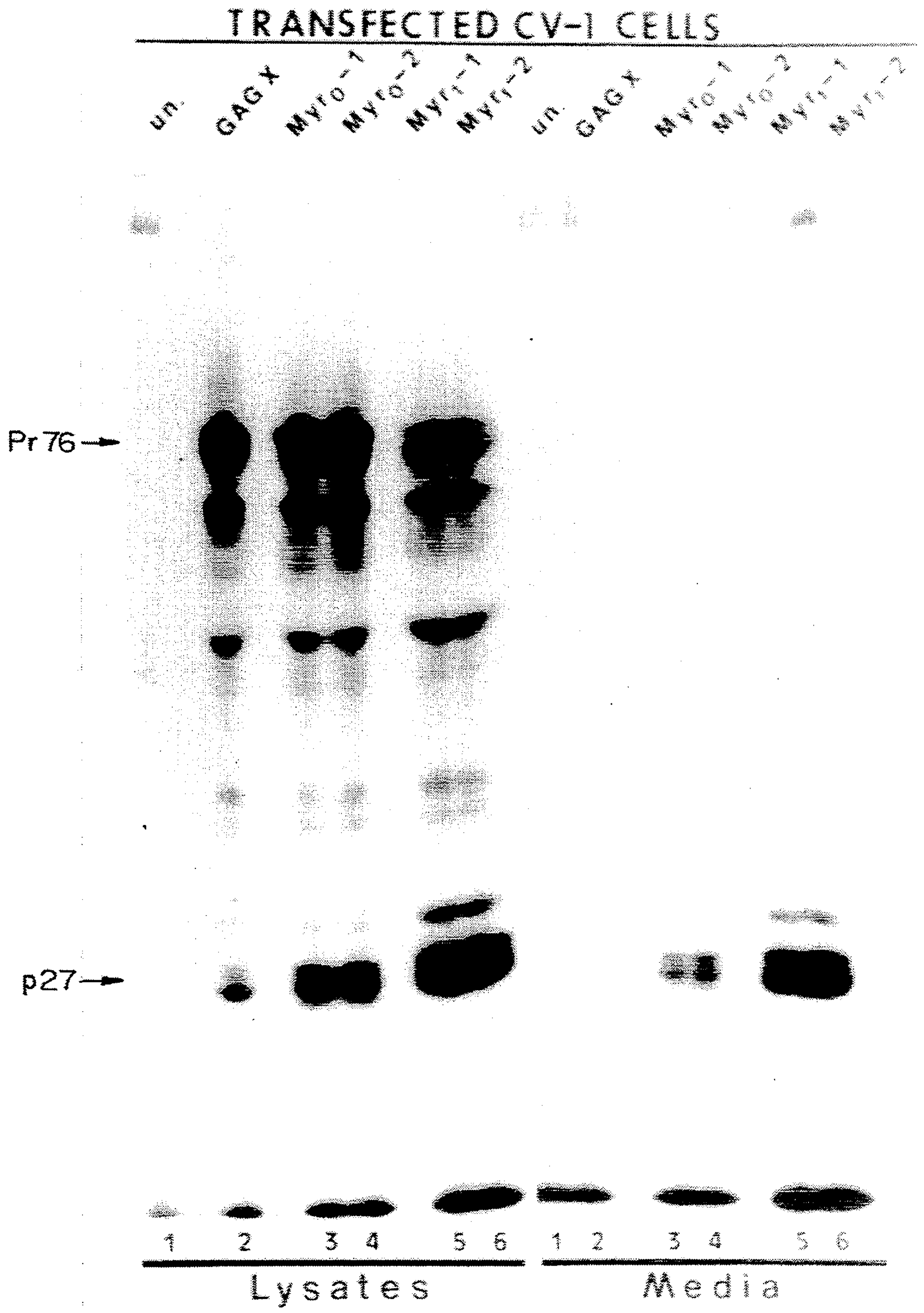
Figure 5:
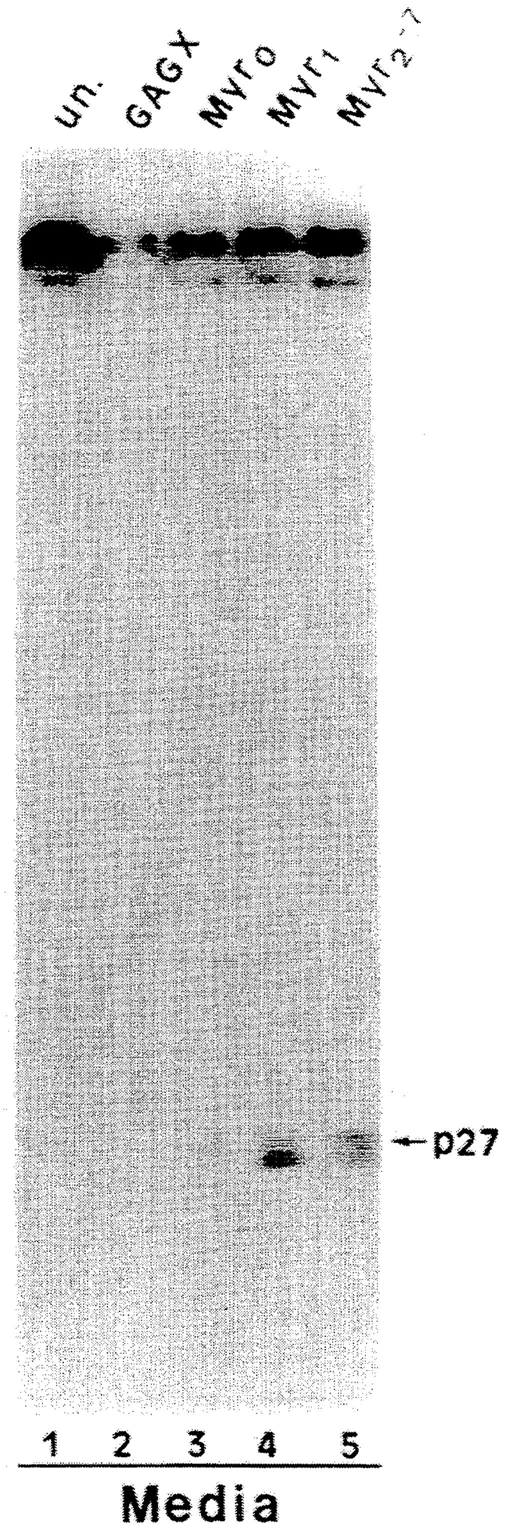
FIG. 5 is an autoradiograph illustrating that a myristylated RSV Gag protein ($Pr76^{myr2}$) is secreted into the culture medium.

The products produced in CV-1 cells were examined after transfection with two clones of pΔSV.Myr$_0$ and two clones of pΔSV.Myr$_1$. Three striking observations were made: First, the products of the wild-type protein (Pr76$^{myr0}$) were released with low efficiency into the CV-1 culture medium (FIG. 4B, lanes 3, 4). This indicates that Pr76 can function in mammalian cells if expressed at high levels. Second, engineering of the p60$^{v\text{-}src}$ myristic acid addition site onto Pr76 enhanced its ability (by 5-fold) to be released from the cell (FIG. 4B, lanes 5 and 6). An identical result was obtained with the point mutation (Glu to Gly) that created Pr76$^{myr2}$ (FIG. 5). In conjunction with the first observation, this suggests that myristic acid is an important component but not the sole determinant for targeting of gag products to the plasma membrane. The third striking result was that processing of Pr76$^{myr0}$ and Pr76$^{myr1}$ in mammalian cells occurred in a manner similar, if not identical, to that of authentic RSV. The five p27-related bands described above for RSV are also seen in the mammalian cell lysates. Furthermore, the processing efficiency is quite high, since almost no intermediates are detected in the medium (FIG. 4B).

Since Pr76$^{gag}$ function in mammalian cells may depend (in part) upon the levels of expression, it was of interest to estimate how much protein is produced by the SV40 vector. For this purpose, the efficiency of transfection was measured using an indirect immunofluorescence assay with anti-p27. Typically, 30% of the CV-1 cells expressed Gag antigens. Taking this efficiency into account, it was calculated that the gag products released into the medium during a 2.5 h labeling period (at 48 h post-transfection) was approximately equal to that released from RSV-infected turkey cells during the same period.

EXAMPLE 5

Myristylated RSV Gag Proteins are Budded from Mammalian Cells

To determine whether Pr76$^{myr1}$ products are released by an actual budding process, their containment within a vital membrane was assessed by trypsin susceptibility. The culture fluid was collected from pΔSV.Myr$_1$-transfected CV-1 cells and pJD100-transfected turkey cells (for comparison) after radiolabeling for 2.5 h with $^{35}$S-methionine in serum-free medium. Any loose cells present in the medium were removed by centrifugation at 15,000 g for 5 min, and the supernatant was immediately divided into six equal portions and processed as follows: One portion received nothing further, a second received 500 µg/ml (final concentration) of soybean trypsin inhibitor, a third received Triton X-100 to 1%, a fourth received 200 µg/ml of trypsin, a fifth received Triton X-100+trypsin, and the sixth received soybean trypsin inhibitor+trypsin. The activity of the trypsin was 11,500 units/mg, and a six-fold excess of soybean trypsin inhibitor was used. All of the samples were incubated for 30 min at room temperature, and then trypsin inhibitor was added to the tubes that had received none. The treated samples were mixed with 5× lysis buffer B for immunoprecipitation. The immunoprecipitates were analyzed by electrophoresis in a 10% SDS-polyacrylamide gel followed by fluorography.

Figures 6A, 6B:
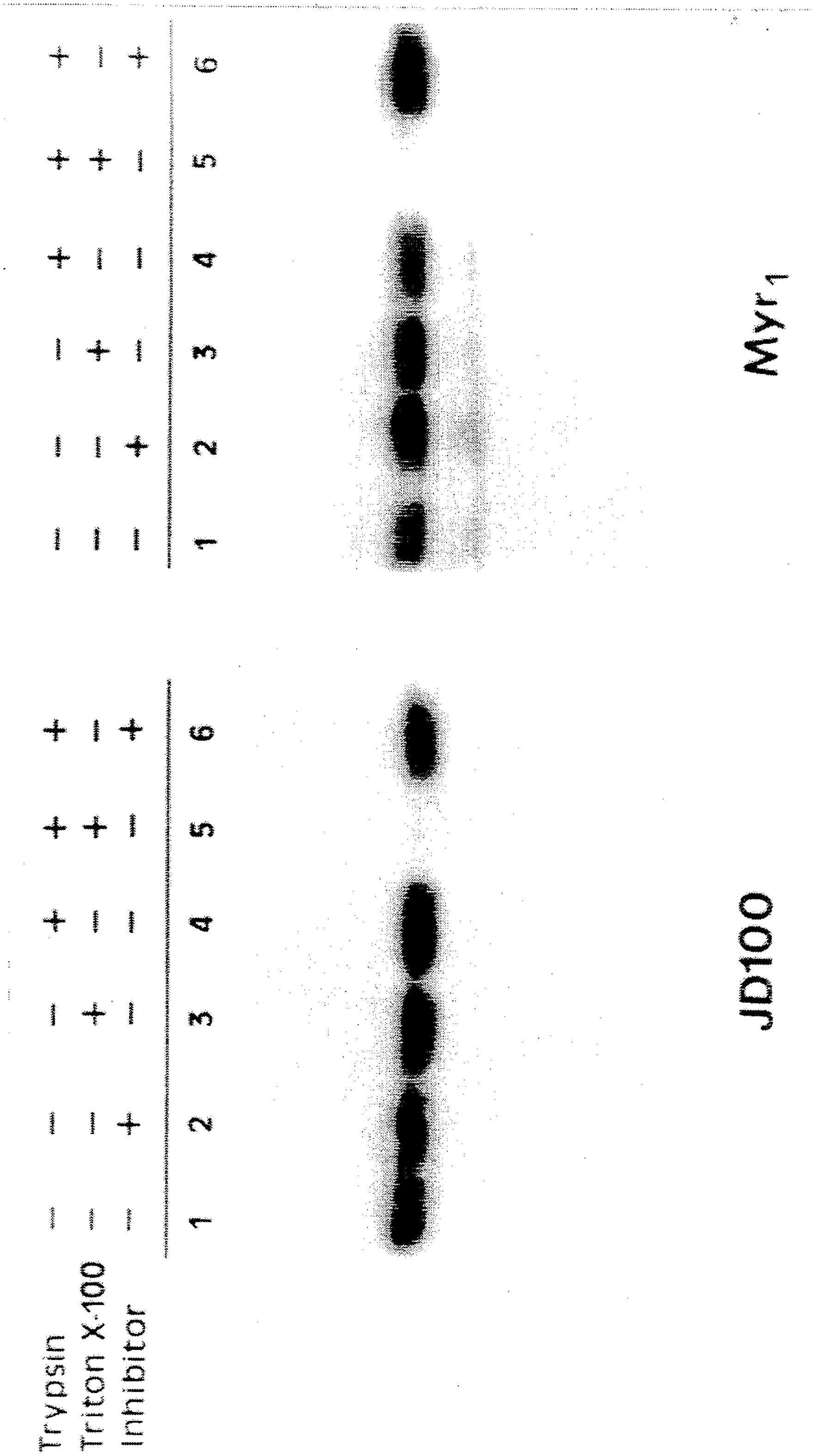
FIGS. 6A and B represent an autoradiograph illustrating that RSV $Pr76^{myr1}$, contained in a membraneous particle is susceptible to trypsin digestion only in the presence of a detergent and not in its absence.

The resulting fluorograph shows that the released products of authentic Pr76$^{gag}$ (FIG. 6A) and Pr76$^{myr1}$ (FIG. 6B) were completely stable during incubations in the presence of nothing (lane 1), trypsin inhibitor alone (lane 2), Triton X-100 alone (lane 3), trypsin (lane 4), and trypsin+inhibitor (lane 6). For both samples, the gag products became susceptible to the protease only when the membrane dissolving agent and trypsin were present together (lane 5).

Further evidence that Pr76$^{myr1}$ products were released within a viral envelope was obtained by sedimentation analysis. It was found that conditions suitable for pelleting authentic RSV (45 min at 70,000 g) also quantitatively pelleted the Myr$_1$ particles out of the CV-1 culture medium. Preliminary experiments also indicate that Myr$_1$ particles have a density in a sucrose gradient that is similar to RSV virions run in parallel gradients. The proteins present in the gradient-purified Myr$_1$ particles include the mature "p27-doublet" which was detectable by Coomassie blue staining after electrophoresis.

EXAMPLE 6

The Amino Terminus of RSV Gag is Needed for Budding

Figure 7:
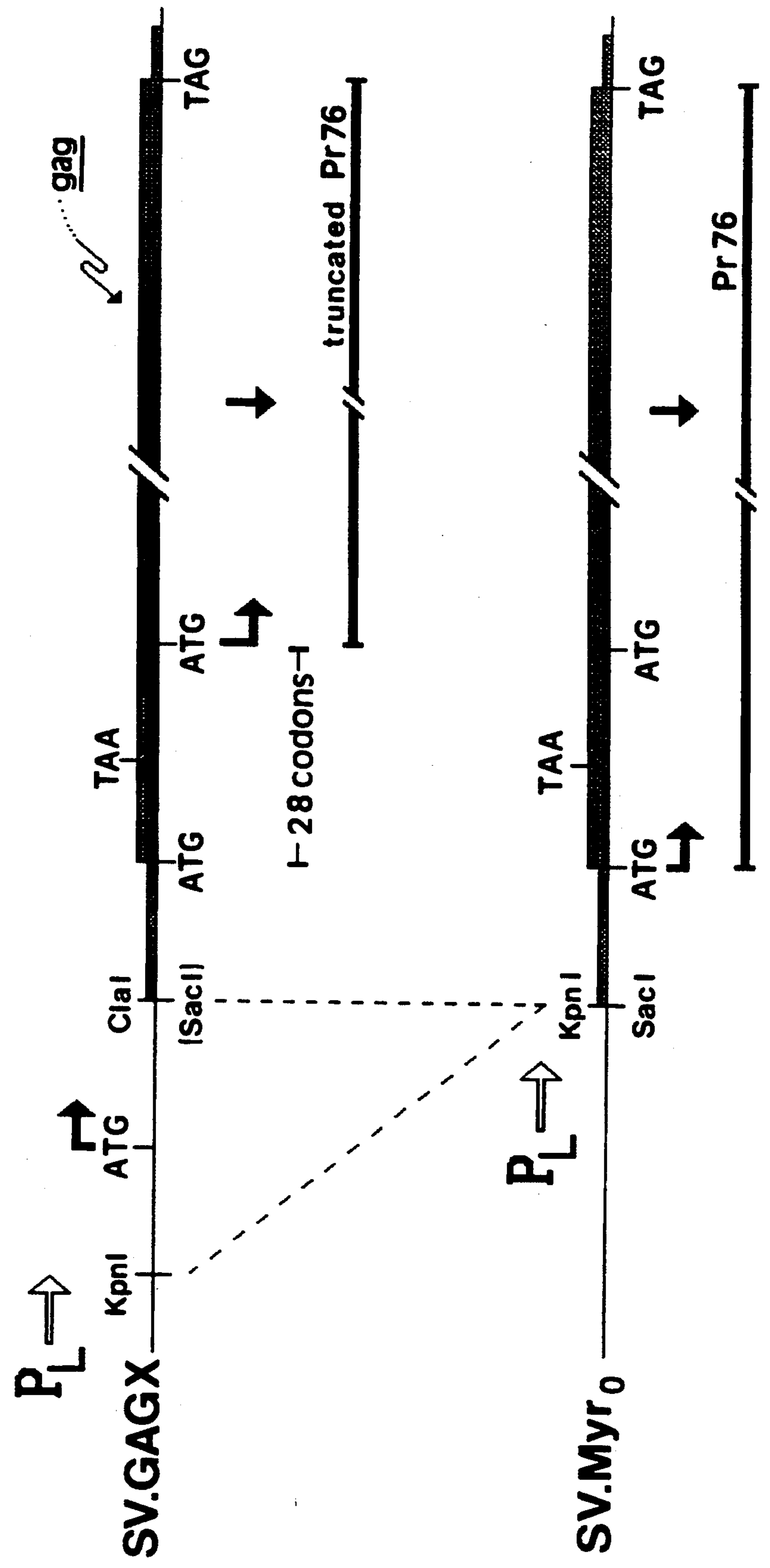
FIG. 7 diagrammatically compares the promoter and 5'-end regions of pΔSV.GAGX and pΔSV.$Myr_0$.

The low level of Pr76$^{myr0}$ found in the culture medium shows that myristylation of Pr76 is not the only requirement for targeting, budding and processing of RSV gag gene products in the mammalian cell. Moreover, from Pr76$^{myr1}$ and Pr76$^{myr2}$, it appears that the precise sequence of the first 10 amino acids of Pr76 is nonessential for these events. To rule out the possibility that the various forms of Pr76 were released by a non-specific, cell blebbing-mechanism, perhaps driven by high expression levels, the product of an SV40-gag vector called pΔSV.GAGX was characterized. This product has an amino-terminal truncation.

pΔASV.GAGX differs from pΔSV.Myr$_0$ (and also pΔSV.Myr$_1$ and pΔSV.Myr$_2$) only by the presence of an additional 52 bp from the SV40 late region. More specifically, the SV40 sequences from KpnI to HpaII are present in a ClaI linker inserted at the junction of SV40 and RSV sequences (FIG. 7). This extra fragment contains the initiation codon for the SV40 agnoprotein which has been found to be used efficiently in SV40 late region-replacement vectors (Perez et al. 1987, J. Virol. 61: 1276–1281). The agnoprotein initiation codon is out-of-frame with the gag initiation codon (nt 380), and translation initiated upstream does not terminate until the latter has been passed. If translation resumes at the next internal methionine codon (nt 464), then Pr76$^{gagX}$ would lack the first 28 amino acids of Pr76.

Figure 8:
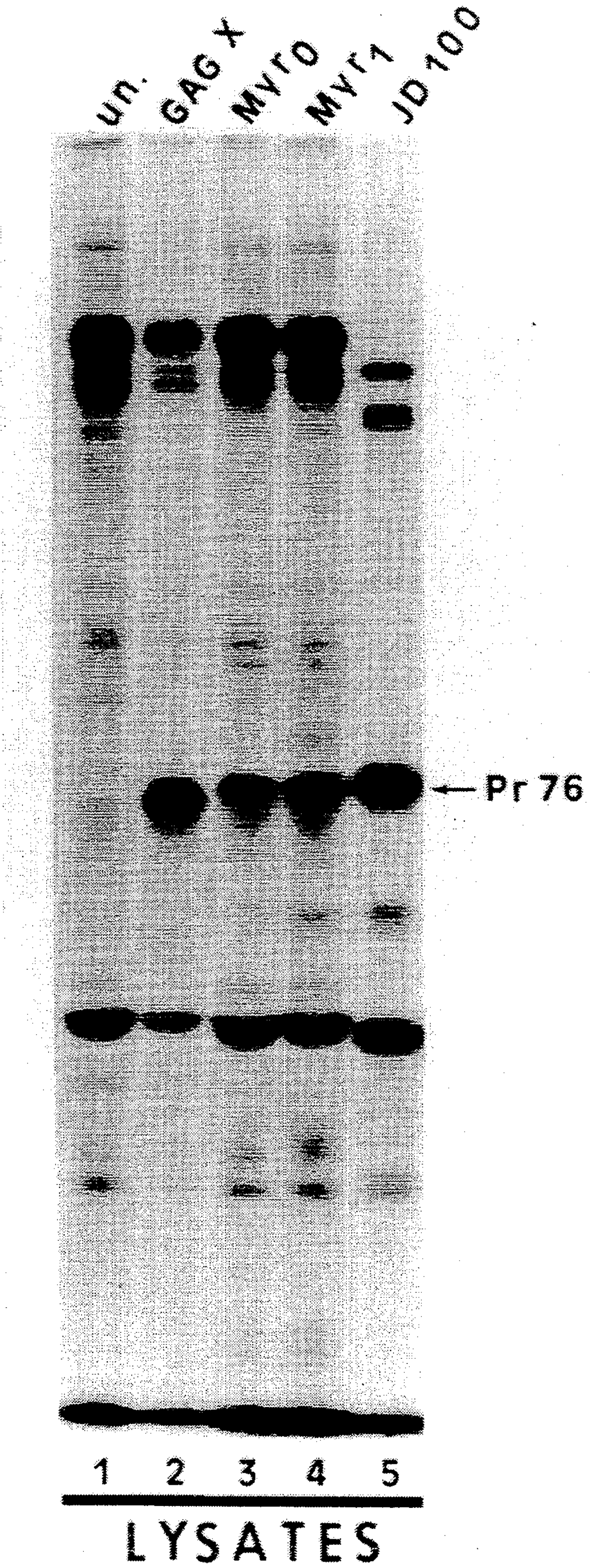
FIG. 8 is an autoradiograph illustrating the Pr76 Gag products of pΔSV.GAGX, pΔSV.$Myr_0$, pΔSV.$Myr_1$ and JD100.

FIG. 8 shows the results of transfecting CV-1 cells with nothing (lane 1), pΔSV.GAGX (lane 2), pΔSV.Myr$_0$ (lane 3), or pΔSV.Myr$_1$ (lane 4) and JD100-infected turkey cells (lane 5) after pulse-labeling with $^{35}$S-methionine. The Gag precursors were collected from cell lysates by immunoprecipitation with anti-p27, electrophoresed in a low concentration (7%) SDS-polyacrylamide gel, and detected by fluorography. Pr76$^{gagX}$ appears to be about 3000 daltons smaller than the other forms of Pr76, consistent with a 28 amino acid truncation. Since another ATG is located only 11 codons downstream (nt 497), the precise site of reinitiation remains unknown in the absence of direct amino acid sequence information; nevertheless, it is clear that Pr76$^{gagX}$ is truncated.

The behavior of Pr76$^{gagX}$ is quite distinct from that of Pr76$^{myr0}$ and Pr76$^{myr1}$. It is poorly released into the medium and poorly processed to give products that migrate at the position of p27 (FIG. 4A and 4B, lane 2). It could be that a mutation elsewhere in gag is responsible for this aberrant behavior but that was ruled out because: i) pASV.GAGX is the parent plasmid for all of the other SV40-gag constructions, and ii) its gag sequence has been shown to be fully functional when returned to the RSV genome. Thus, the inability of Pr76$^{gagX}$ to be released into the medium clearly indicates that the amino-terminus of Pr76 is required for specific events during particle formation, and that the highly expressed proteins are not blebbing into the medium.

EXAMPLE 7

A Truncated Pr76$^{myr1}$ is Capable of Budding

The construction of the vectors pΔSV.Myr$_{1A}$ pΔSV.myr$_{1B}$ and pΔSV.Myr$_{1C}$ was described in Example 2.

Two clones corresponding to each of these shortened gag DNAs were transfected into CV-1 cells, and 48 h later the truncated proteins were labeled for 2.5 h with $^{35}$S-methionine. After labeling, the medium was removed from the cells (and saved) and cell lysates were prepared. RSV gag proteins were collected by immunoprecipitation from the cell lysates and the medium using antibodies against p27. The immunoprecipitates were analyzed by electrophoresis on 10% SDS-polyacrylamide gel and fluorography.

The results indicate (FIG. 9) that as previously shown, non-truncated Pr76$^{Myr1}$ is produced in the transfected cells (uppermost band in lane 2) and gives rise to several processing intermediates and p27 (the darkest band near the bottom of lane 2). The Pr76$^{Myr1}$ processing products are released into the medium (lane 10). Controls (untransfected cells) show non-specific bands in the cell lysate (lane 1), none of which are present in the medium (lane 9).

The results further indicate that a portion of the pr76$^{Myr1}$ C-terminus can be deleted without impairing targeting or budding. Processing is eliminated because p15 (encoding the protease) has been at least partially deleted by C-terminal truncations.

Figure 9A:
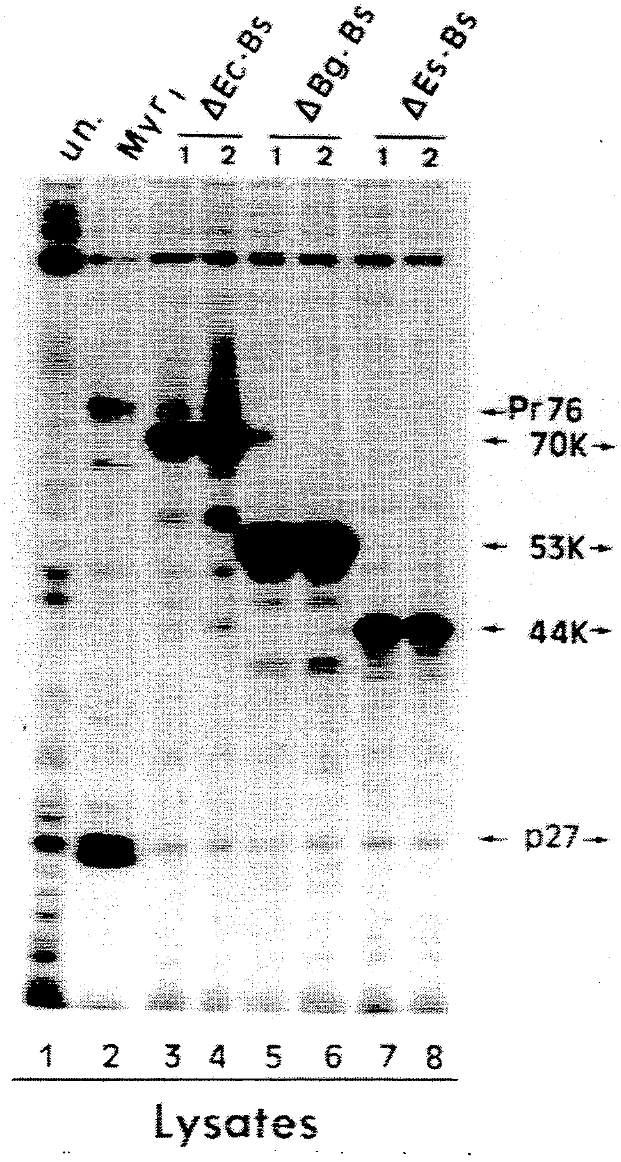
FIG. 9 is an autoradiograph illustrating that $Pr76^{myr1}$ proteins with C-terminal deletions are produced by the corresponding pΔSV.$Myr_1$ expression vectors, and further defines the limits of C-terminal deletions that allow truncated $Pr76^{myr1}$ derivatives to be produced in membraneous particles.
Figure 9B:
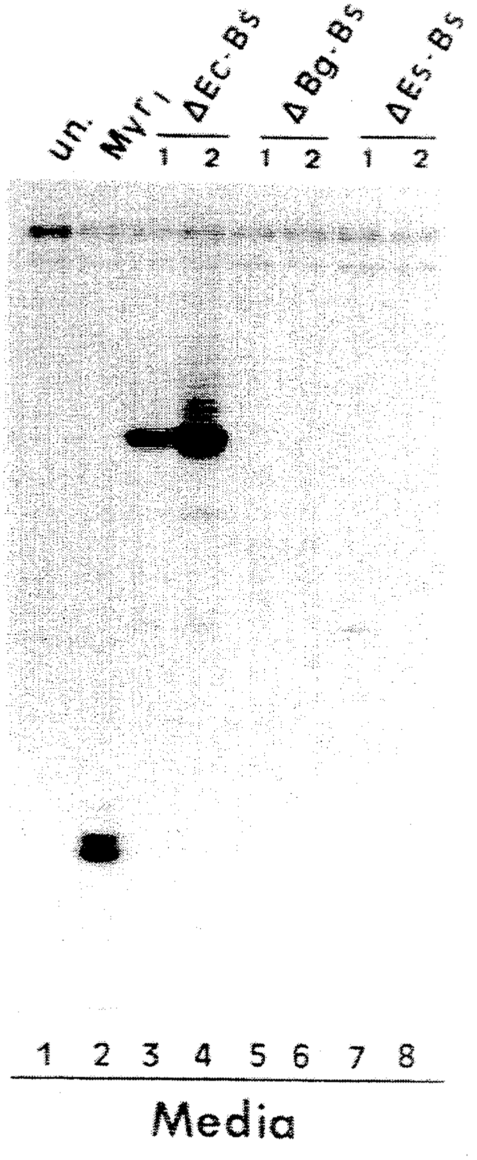

As seen in FIG. 9, lysates prepared from cells transfected with pΔSV-Myr$_{1A}$ (lanes 3, 4), pΔSV.Myr$_{1B}$ (lanes 5, 6) and pΔSV.Myr$_{1C}$ (lanes 7, 8) produce truncated Pr76$^{Myr1A}$ and pr76$^{Myr1B}$ and Pr76$^{Myr1C}$, respectively. Of these three, only Pr76$^{Myr1A}$ is found in the culture medium (lanes 10, 11). The other two products are not detected (lanes 13–16).

This example illustrates that truncations of Pr76$^{Myr1}$ extending at least to the amino acid position corresponding to the EcoRI site in that gene, but not as far as the BglII site, can be released in membraneous particles.

EXAMPLE 8

Deletions in Pr76$^{myr1}$ Define Three Domains of RSV Gag Need for Budding

To systematically determine the Pr76$^{myr1}$ sequences required for particle formation, a series of deletions were constructed in the Pr76$^{myr1}$ coding region of pΔSV.Myr$_1$ as described in Example 2 and as depicted in FIG. 12. (The gaps indicate deleted sequences.) DNA encoding these deletion derivatives was transfected into cultured cells and tested for budding as described in Example 7. Deletion mutants depicted in FIG. 12 by solid lines were capable of budding; those which could not bud are depicted by non-solid lines. From this analysis three regions of the Pr76$^{myr1}$ protein appear to be essential for budding: amino acids 1–8, 84–174 and 417–515 (gray shading in FIG. 12).

EXAMPLE 9

Release in Fusion Proteins in Membraneous Particles

The construction of plasmids pSV.MyCYE and pSV.MyCYC1 is described in Example 2.

Figure 10A:
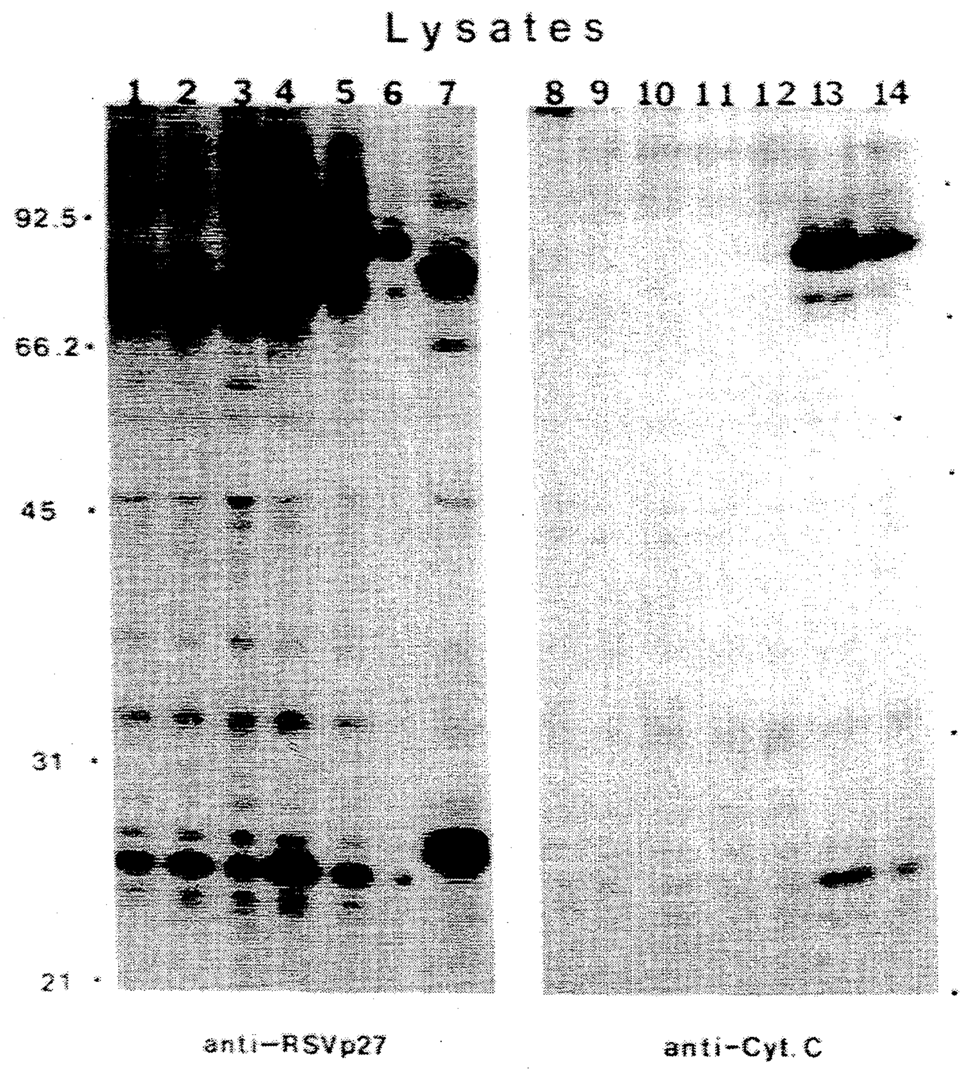
FIGS. 10A and B represent an autoradiograph illustrating that a gene fusion of the RSV $myr_1$ allele and the yeast cyc1 gene produce fusion proteins released into the culture medium of CV-1 cells.
Figure 10B:
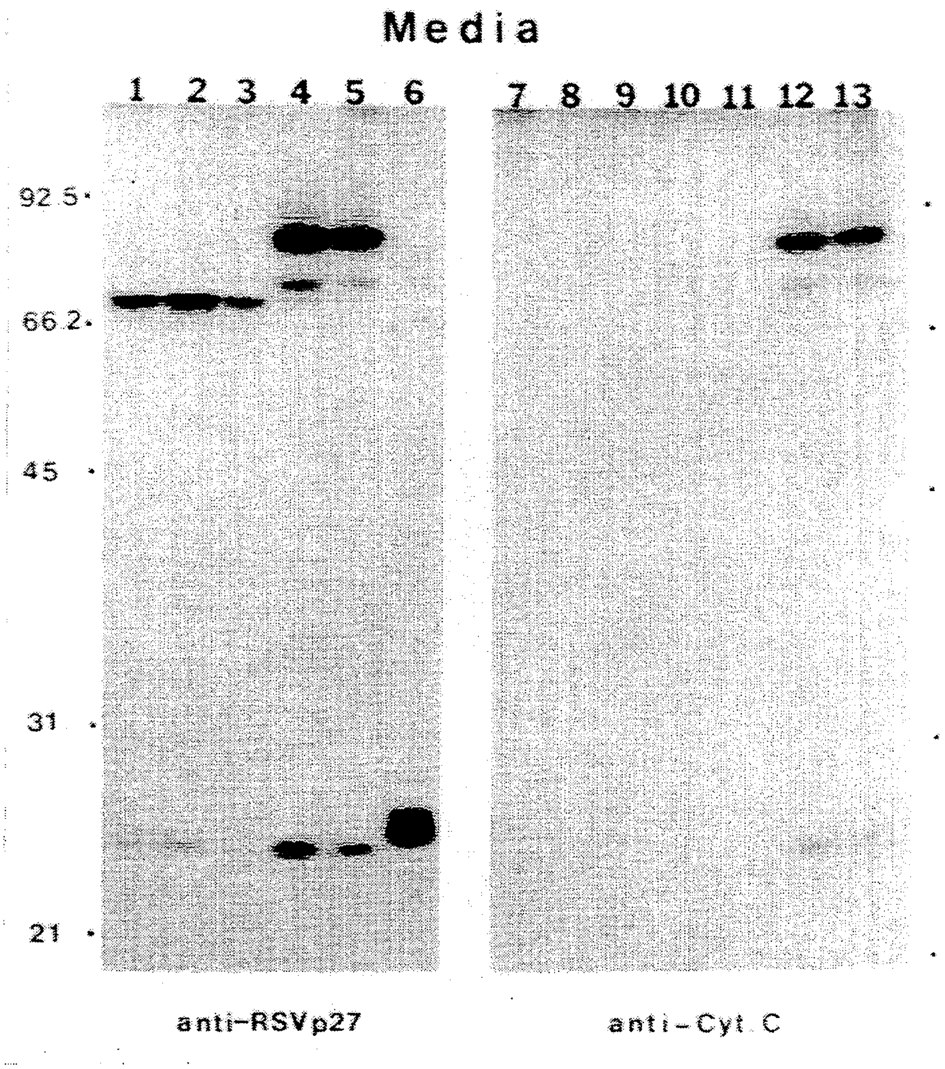

To determine if Pr76$^{Myr1}$ fusion proteins are expressed and budded from the mammalian cells, CV-1 cells were transfected with pSV.MyCYE and pSV.MyCYC1. Cell lysates and culture medium from several clones from each transfection together with controls were analyzed for gag-cycl gene fusion products by immunoprecipitation with anti-p27 or anti-cytochrome c antibodies. The fusion products of pSV.MyCYE were not expected to react with anti-cytochrome c antibodies. The cell lysate products in the medium are shown in FIG. 10A, and the budded products in the medium are shown in FIG. 10B. The controls (mock infection: FIG. 10A, lanes 7, 9, and FIG. 10B, lane 7; pΔSV.Myr$_1$: FIG. 10A, lanes 7, 9, and FIG. 10B, lanes 6, 8) were the same as previous results using anti-p27 antibodies for immunoprecipitation. These controls establish that anti-cytochrome c antibody does not crossreact with Pr76$^{Myr1}$.

The three pSV.MyCYE-derived clones containing an out-of-frame cycl gene produce truncated proteins that reacted only with anti-p27 serum (FIG. 10a, lanes 1, 2, 3) and were released from the cell by budding (FIG. 10B, lanes 1, 2, 3). Neither the lysates (FIG. 10a, lanes 10, 11, 12) or the cell medium from these cells (FIG. 10b, lanes 9, 10, 11) contain antigens that react with anti-cytochrome C serum.

The cells transfected with the in-frame pSV.MyCYC1-derived gene fusions produced proteins that were larger than $Pr76^{Myr1}$ and that reacted with both the anti-p27 serum (FIG. 10A, lanes 4, 5) and the anti-cytochrome C serum (FIG. 10A, lanes 13, 14). Lane 6 in FIG. 10A is a dilution of the sample in lane 5. The larger proteins were released into the culture medium and reacted with both the anti-p27 serum (FIG. 10B, lanes 4, 5) and the anti-cytochrome C serum (FIG. 10B, lanes 12, 13). Hence, the $Pr76^{Myr1}$-CYC fusion protein was budded into the culture medium.

The particles released form the transfected cells also contain two small, co-migrating proteins one of which reacted with the anti-p27 serum (FIG. 10B, lanes 4, 5) and the other of which reacted with the anti-cytochrome c serum (FIG. 10B, lanes 12, 13). Because the truncated $Pr76^{Myr1}$ protein lacks the viral protease that is implicated in its processing, these cleavage products indicate that a cellular protease may have access to fusion proteins during budding.

EXAMPLE 10

$Pr76^{Myr1}$ and $Pr76^{Myr1}$-CYC1 are Packaged

Figure 11:
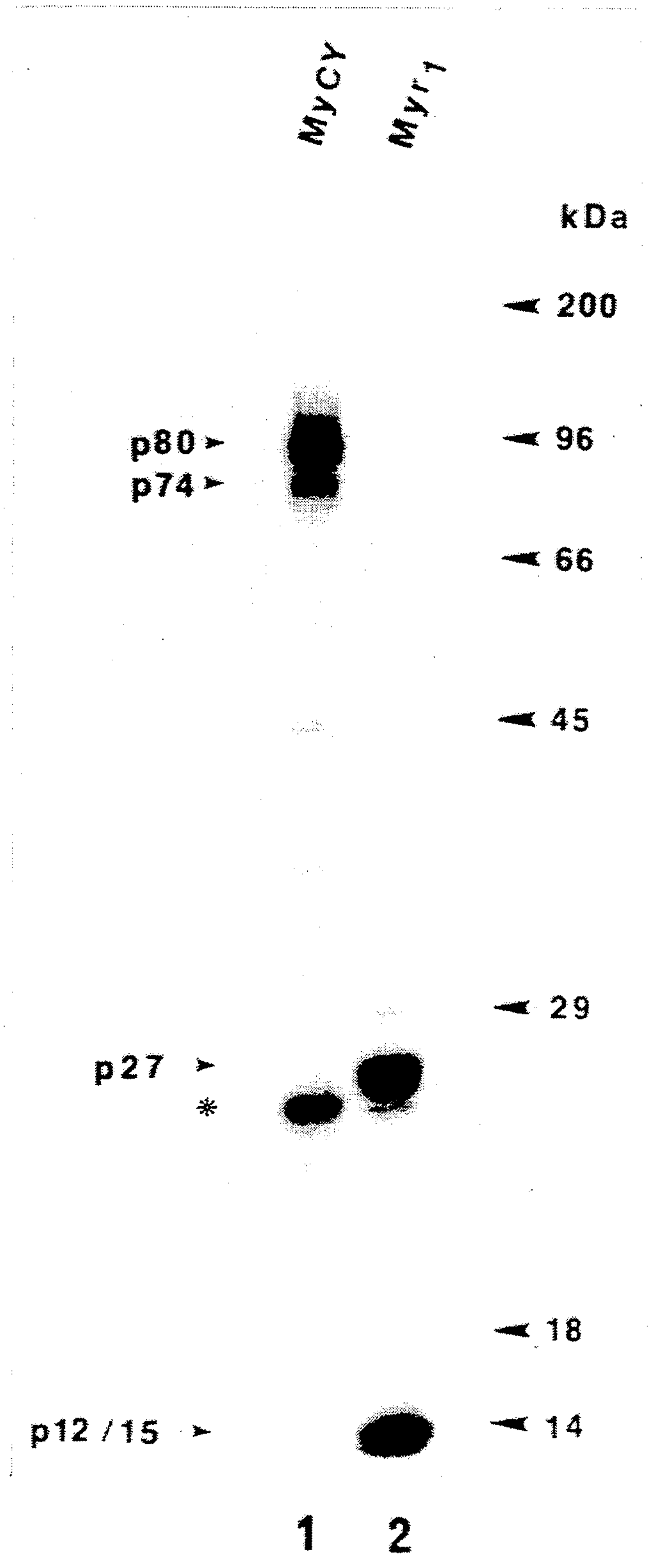
FIG. 11 is an autoradiograph illustrating that $Pr76^{Myr1}$ and the fusion of $Pr76^{Myr1}$-CYC1 are produced in COS-1 cells, released in membraneous particles and processed.

To verify that $Pr76^{Myr1}$ and $Pr76^{Myr1}$-CYC1 are secreted in particles and further to show that the mammalian cell lines can produce and package RSV gag gene products, COS-1 cells were transfected with pΔSV.$Myr_1$ and pSV.MyCYC1. The transfected cells were metabolically labeled 48 h post-transfection with $^{35}$S-methionine for 12 h. The culture medium was harvested, cleared of cellular debris by low speed centrifugation, and the particles were then purified by high speed centrifugation (15,000, 1 h) through a 5%-sucrose cushion. The pellets were resuspended in lysis buffer and 50,000 CPM/sample were analyzed on a 12.5% SDS-polyacrylamide gel. An autoradiograph of the gel (FIG. 11) indicates that $Pr76^{Myr1}$ (lane 2) and $Pr76^{Myr1}$-CYC1 (lane 1) were sedimented and processed. $Pr76^{Myr1}$ was processed to the expected p27, p15 and p12 products. $pr76^{Myr1}$CYC1 was partially processed releasing a protein slightly smaller than p27 that was immunoprecipitatable with anti-cytochrome c antibody (compare with FIG. 10B, lanes 12, 13).

EXAMPLE 11

Particle Formation by Myristylated RSV Gag Protein is Highly Efficient in Avian and Murine Cells The RSV Gag protein drives budding and membrane particle formation in simian COS-1 and CV-1 cell lines when myristate is added to its amino terminus- To test whether myristylated RSV Gag protein efficiently forms particles in other cell lines, the $myr_1$ allele was placed under the control of the murine leukemia virus (MLV) LTR promoter since this promoter functions in a broad range of species, including avian and murine cells.

The vector chosen for $myr_1$ expression pDOL.ATG- provides cloning sites flanked by MLV LTR sequences, a neomycin antibiotic resistance gene (neo), a bacterial origin of replication and the gene for the polyoma large T antigen.

Figure 13:
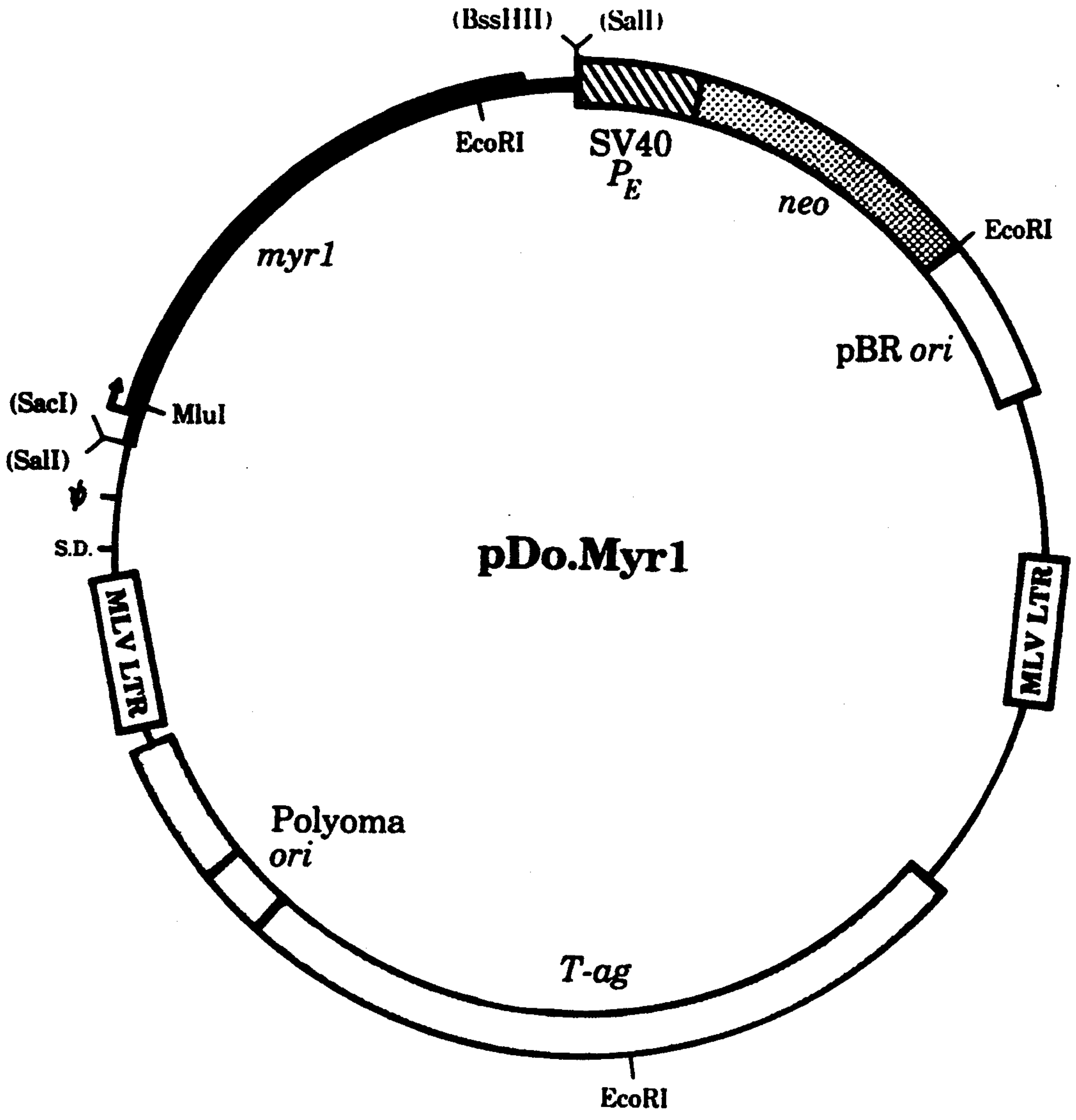
FIG. 13 is a schematic diagram illustrating the expression vector used for expressing $Pr76^{Myr1}$ in murine and avian cells. The $myr_1$ allele is represented by the thick, black line in which the start of the coding sequence is marked with an arrow. The unique MluI site was created in altering the 5'-end so that is encodes the first 10 amino acids of $p60^{v\text{-}src}$. The SacI-BssHII fragment was cloned from p SV.Myr1 into the SalI site, thereby destroying the sites indicated in parentheses. The leftmost LTR serves as the promoter for transcription of $myr_1$. pDo. Gag is identical to this plasmid except that it contains the wild-type RSV gag gene.

The $myr_1$ allele was excised from pΔSV.Myr1 using SacI and BssHII, purified by agarose gel electrophoresis, and ligated into pDOL.ATG- at its unique SalI site after making the DNA ends blunt using the Klenow fragment of DNA polymerase I. The plasmids were propagated in *E. coli* strain DH-1 and selected on LB agar plates containing kanamycin (25 μg per ml). A recombinant bearing the $myr_1$ allele in the proper orientation relative to the LTR promoter was obtained and named pDo.Myr1 (FIG. 13). pDo.Gag is a control plasmid in which the wild-type gag gene was inserted into the same vector at the SalI site.

Initial characterizations of pDo. Gag and pDo.Myr1 were carried out by transient expression assays in murine NIH 3T3 cells. Dishes (35 mm) of 3T3 cells were transfected with 5 μg of DNA using the DEAE-dextran method followed by a chloroquine treatment, as described (Wills et al., 1984). Two days after transfection, the cultures were labeled with [$^{35}$S]methionine for 2.5 h and partitioned into medium and cell lysate fractions. The labeled RSV Gag proteins were immunoprecipitated from the detergent-treated samples using rabbit anti-RSV antibodies, separated by electrophoresis in 12% SDS-polyacrylamide gels, and detected by fluorography.

Figures 14A, 14B:
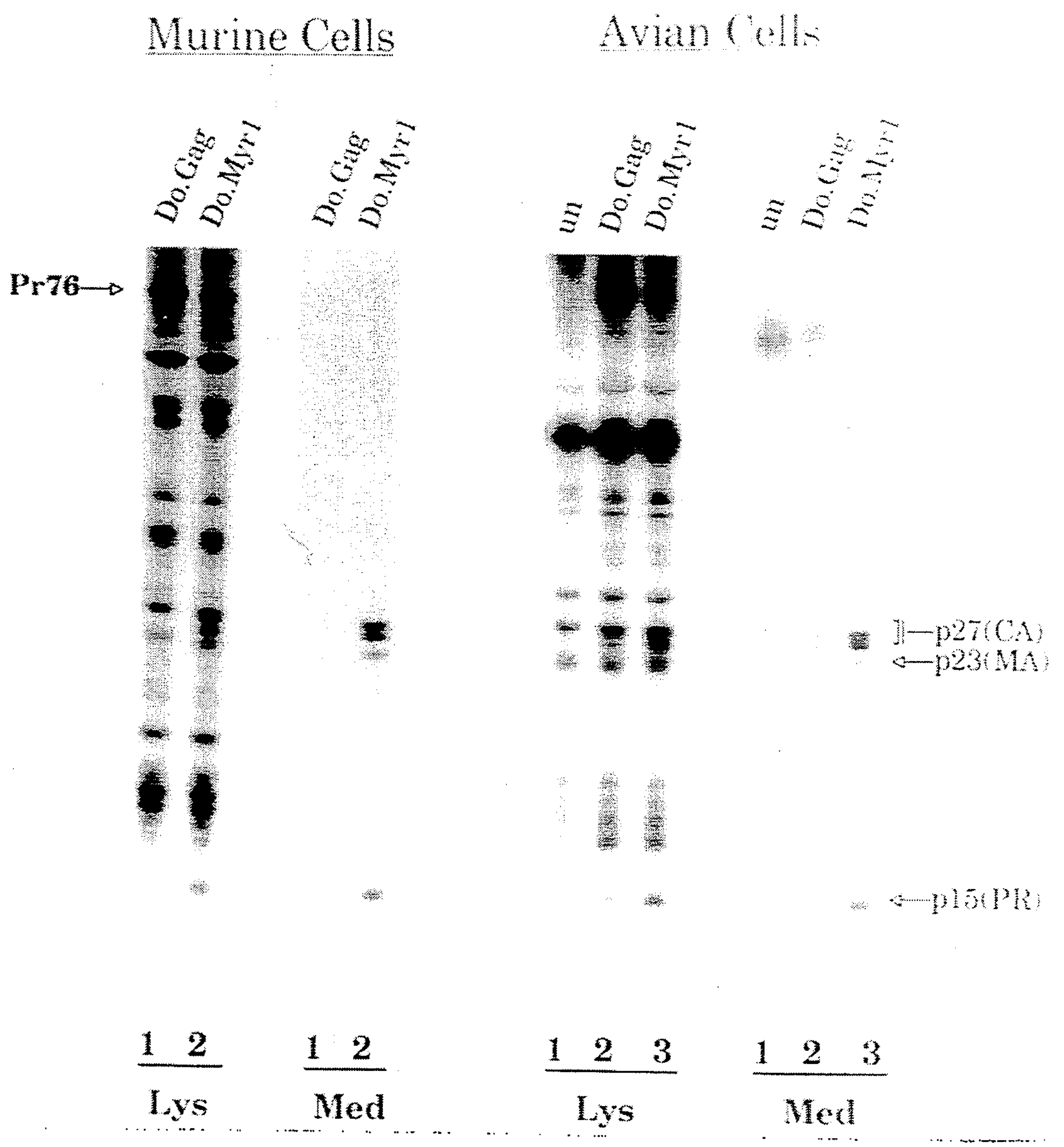
FIGS. 14A and B demonstrate expression of myristylated and non-myristylated Gag proteins in murine and avian cells. (A) Murine (3T3) cells were transfected with pDo.Gag (lane 1) or pDo.Myr1 (lane 2). Positions for $Pr76^{gag}$, p27 (CA), p23 (MA), and p15 (PR) are indicated. (B) Turkey embryo fibroblasts were transfected with no DNA (lane 1), pDo.Gag (lane 2), or pDo.Myr1 (lane 3).

For both constructs, a Gag precursor of about 76 kDa was detected in the cell lysates (FIGS. 14A and B). The non-myristylated $Pr76^{gag}$ produced by pDo.Gag seemed to accumulate to a greater extent within the cell than the myristylated $Pr76^{Myr1}$ produced by pDo.Myr1 (lysate lanes 1 and 2, respectively). This accumulation presumably is due to reduced ability of the pDo.Gag product to form particles relative to that of the pDo.-Myr1 product (compare media lanes 1 and 2). The Gag-related proteins present in the Myr1 particles correspond to the mature cleavage products derived from Pr76, i.e., proteins MA, CA, NC, PR. The same cleavage products were observed in the medium from the cells transfected with pDo.Gag; however, these bands are barely visible on the exposure presented in FIGS. 14A and B. Untransfected cells and cells transfected either with pDOL.ATG- or with a plasmid bearing the gag gene in the wrong orientation revealed only background bands.

The transient expression assays were repeated as above using turkey embryo fibroblasts (see FIG. 14B). Again, the $Pr76^{gag}$ produced by pDo.Gag accumulated in the cells relative to $Pr76^{Myr1}$ produced by pDo.Myr1 (lysate lanes 2 and 3). However, the level of particle formation obtained with $Pr76^{myr1}$ in avian cells was increased relative to that obtained with non-myristylated $Pr76^{gag}$ (media lanes 2 and 3). To ensure these particles were not the result of an endogenous virus, an uninfected control was included which proved to be negative (lysate and media lanes 1). It was surprising that the $Pr76^{myr1}$ produced higher levels of particles relative to the wild-type non-myristylated protein in its native cell type. The pDo.Myr1 construct is thus useful for production of myristylated Gag fusion proteins in a variety of cell types.

What is claimed is:

1. A fusion protein comprising a first domain, wherein said first domain is a retrovirus Gag protein comprising at least amino acid residues 1-8, 84-174 and 417-515 of $Pr76^{myr1}$, wherein said first domain is adapted to covalently bind myristic acid and which permits a host cell to produce a fusion protein in a membranous particle, and a second domain, wherein said second domain is a heterologous protein.

2. The fusion protein of claim 1 comprising a third domain, wherein said domain is a proteolytic cleavage site and is located between said first and said second domains.

3. A membranous particle which comprises a membrane envelope and a fusion protein, wherein said fusion protein comprises a first domain, wherein said first domain is a retrovirus Gag protein comprising at least amino acid residues 1–8, 84–174 and 417–515 of $Pr76^{myr1}$ and wherein said first domain is adapted to covalently bind myristic acid, and which permits a host cell to produce a fusion protein in a membranous particle and a second domain, wherein said second domain is a heterologous protein.

4. The particle of claim 3 wherein said fusion protein contains a proteolytic cleavage site between said gag protein and said heterologous protein.

5. The membranous particle of claim 3 or 4 wherein the particle is admixed with a pharmaceutically acceptable carrier.

6. In a method of purifying a fusion protein, the improvement comprising isolating said fusion protein in the membraneous particle of claim 3.

7. A membranous particle containing a fusion protein wherein said membranous particle is produced by:

(a) transforming a cell with a replicable expression vector which comprises a retrovirus gag gene adapted to permit a host cell to produce said fusion protein in a membranous particle, wherein said gag gene is comprised of the coding sequence for at least amino acid residues 1–8, 84–174 and 417–515 of $Pr76^{myr1}$, and which encodes a myristic acid addition site and wherein said gag gene is fused to a heterologous gene or part thereof to form a hybrid gene operably linked to one or more nucleotide sequence capable of effecting expression of said hybrid gene;

(b) cultivating said cell for a time under conditions sufficient to express said fusion protein in a membranous particle; and (c) recovering said membranous particles.

* * * * *

UNITED STATES PATENT AND TRADEMARK OFFICE

CERTIFICATE OF CORRECTION

PATENT NO. : 5,378,806

DATED : January 3, 1995

INVENTOR(S) : John W. Wills, et al.

It is certified that error appears in the above-indentified patent and that said Letters Patent is hereby corrected as shown below:

On the Title Page, Item: [19] and [75]: "Willis" should read --Wills--

On the Title Page, Item [56], under "OTHER PUBLICATIONS", line 4: "Mruine" should read --Murine-- and Column 1, line 47: "arian" should read --avian--

Column 2, lines 43-44: "co-transitionally" should read --co-translationally--

Column 5, line 36: after "RSV" insert --gag--

Column 5, lines 50 & 52: after "pSV" insert --.--

Column 6, line 57: "vital" should read --viral--

Column 7, line 52: "vital" should read --viral--

Column 8, line 8: "arian" should read --avian--

UNITED STATES PATENT AND TRADEMARK OFFICE
CERTIFICATE OF CORRECTION

PATENT NO. : 5,378,806
DATED : January 3, 1995
INVENTOR(S) : John W. Wills, et al.

It is certified that error appears in the above-indentified patent and that said Letters Patent is hereby corrected as shown below:

Column 10, line 36: "c,f" should read --of--
Column 10, line 39: "Of" should read --of--
Column 10, line 41: "replicahie" should read --replicable--
Column 10, line 58: delete "3"
Column 11, line 33: "retrovital" should read --retroviral--
Column 11, line 52: "pertinacious" should read --proteinaceous--
Column 11, line 55: "arian" should read --avian--
Column 13, line 3: "propagaged" should read —propagated —.
Column 15, line 23: "Unq" should read --Ung--
Column 15, line 58: "free" should read --frame--
Column 16, line 30: "pASV" should read p∆ SV —.
Column 16, line 33: "myr2" should read --$myr_2$--

UNITED STATES PATENT AND TRADEMARK OFFICE

CERTIFICATE OF CORRECTION

PATENT NO. : 5,378,806

DATED : January 3, 1995

INVENTOR(S) : John W. Wills, et al.

It is certified that error appears in the above-indentified patent and that said Letters Patent is hereby corrected as shown below:

Column 17, lines 35, 36, 41, 55 & 60: "pSV-" should read --pSV.--

Column 18, line 46: delete "{"

Column 19, line 15: "Pt76" should read --Pr76--

Column 20, line 10: "vital" should read --viral--

Column 20, line 65: after "blebbing" delete -- - --

Column 21, line 1: "pΔASV" should read --pΔSV--

UNITED STATES PATENT AND TRADEMARK OFFICE

CERTIFICATE OF CORRECTION

PATENT NO. : 5,378,806

DATED : January 3, 1995

INVENTOR(S) : John W. Wills, et al.

It is certified that error appears in the above-indentified patent and that said Letters Patent is hereby corrected as shown below:

Column 22, line 11: "pr76" should read --Pr76--

Column 23, line 40: "pr76" should read --Pr76--

Column 23, line 50: "terminus-" should read --terminus.--

Column 24, line 60, Claim 1: after "$Pr76^{myr1}$," insert --and--

Signed and Sealed this

Thirteenth Day of February, 1996

Attest:

BRUCE LEHMAN

*Attesting Officer*

*Commissioner of Patents and Trademarks*